United States Patent
Spies et al.

(10) Patent No.: US 7,666,417 B2
(45) Date of Patent: Feb. 23, 2010

(54) METHODS AND COMPOSITIONS FOR TREATING AUTOIMMUNE DISEASES OR CONDITIONS

(75) Inventors: Thomas Spies, Seattle, WA (US); Veronika Spies, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 10/898,003

(22) Filed: Jul. 23, 2004

(65) Prior Publication Data

US 2005/0158307 A1 Jul. 21, 2005

Related U.S. Application Data

(63) Continuation-in-part of application No. PCT/US03/12299, filed on Apr. 22, 2003.

(51) Int. Cl.
A61K 39/395 (2006.01)
(52) U.S. Cl. .................... 424/143.1; 424/145.1
(58) Field of Classification Search ........................ None
See application file for complete search history.

(56) References Cited

U.S. PATENT DOCUMENTS

| | | | |
|---|---|---|---|
| 5,698,195 A * | 12/1997 | Le et al. ................... | 424/133.1 |
| 6,262,244 B1 | 7/2001 | Houchins et al. ........... | 536/23.5 |
| 6,458,350 B1 | 10/2002 | Cosman et al. ............ | 424/85.1 |
| 6,653,447 B1 | 11/2003 | Cosman et al. ............ | 530/350 |
| 6,737,249 B1 * | 5/2004 | Adams et al. .............. | 435/69.1 |
| 2002/0187151 A1 | 12/2002 | Raulet et al. .............. | 424/155.1 |
| 2003/0095965 A1 | 5/2003 | Van Beneden et al. ... | 424/141.1 |
| 2003/0165835 A1 | 9/2003 | Spies et al. ..................... | 435/6 |
| 2003/0171280 A1 | 9/2003 | Soderstrom ................... | 514/12 |
| 2004/0115198 A1 | 6/2004 | Spies et al. .............. | 424/145.1 |
| 2005/0233391 A1 | 10/2005 | Spies et al. ................ | 435/7.23 |
| 2006/0280755 A1* | 12/2006 | Baron et al. ............. | 424/204.1 |
| 2007/0077241 A1 | 4/2007 | Spies et al. .............. | 424/133.1 |
| 2007/0248607 A1* | 10/2007 | Spies et al. .............. | 424/141.1 |

FOREIGN PATENT DOCUMENTS

| | | |
|---|---|---|
| WO | WO 98/19167 | 5/1998 |
| WO | WO 01/71005 | 9/2001 |
| WO | WO 02/068615 | 9/2002 |
| WO | WO 03029436 A2 * | 4/2003 |
| WO | WO 03/089616 | 10/2003 |

OTHER PUBLICATIONS

Schrambach et al., PLoS ONE. Jun. 2007 132:e518.*
Diefenbach et al., (2002) Nat Immunol. 3(12):1142-9.*
Goronzy et al., Curr Opin Rheumatol. May 2004;16(3):212-7.*
Gratama et al., Cytometry. Apr. 15, 2002;50(2):92-101.*
Cardozo et al., Diabetologia. Feb. 2003;46(2):255-66.*
Martinelli et al., Gastroenterology. Jun. 1996;110(6):1791-802.*
Marshall et al., J Autoimmun. Feb. 2004;22(1):1-11.*
Luzza et al., FEMS Immunol Med Microbiol. Jun. 1999;24(2):233-8.*
Bergman et al., "Gastric Autoimmunity", pp. 1-19, In Heliobacter pylori Physiology and Genetics, Mobley et al., eds., ASM Press, 2001.*
Saegusa et al., J Immunol. Aug. 15, 2000;165(4):2251-7.*
Janeway et al., Immunobiology, 5th Ed., Garland Science, pp. 94-105 (2001).*
Rudikoff et al., Proc. Natl. Acad. Sci. USA, 79: 1979-1 983, Mar. 1982.*
Colman P. M., Research in Immunology, 145:33-36, 1994.*
Ziwei Huang, Pharmacol Ther. Jun. 2000;86(3):201-15.*
Whitty et al., Chem. Biol. Apr. 1999;6(4):R107-18.*
S.J. van Deventer, Best Pract Res Clin Gastroenterol. Feb. 2003;17(1):119-30.*
Strom et al., Therapeutic Immunology edited by Austen et al., Blackwell Science, Cambridge, MA, 1996, pp. 451-456.*
Sakai et al., Gastroenterology, Jun. 1998;114(6):1237-43.*
Bauer et al., "Activation of NK cells and T cells by NKG2D, a receptor for stress-induced MICA," *Science*, 285(5428)727-729, 1999.
Chapman et al., "CD11b+CD28-CD4+ human T cells: activation requirements and association with HLA-DR alleles," *J. Immunol*, 157(11):4771-4780, 1996.
Das et al., "MICA engagement by human Vγ2Vδ2 T cells enhances their antigen-dependent effector function," *Immunity*, 15:83-93, 2001.
Feldman et al., "Perspectives of arterial gene therapy for the prevention of restenosis," *Cardiovasc. Res.*, 32:194-207, 1996.
Groh et al., "Tumour-derived soluble MIC ligands impair expression of NKG2D and T-cell activation," *Nature*, 419:734-738, 2002.
Groh et al., "Broad tumor-associated expression and recognition by tumor-derived γδ T cells of MICA and MICB," *Proc. Natl. Acad. Sci., USA*, 96:6879-6884, 1999.
Groh et al., "Cell stress-regulated human major histocompatibility complex class I gene expressed in gastrointestinal epithelium," *Proc. Natl. Acad. Sci., USA*, 93:12445-12450, 1996.
Groh et al., "Costimulation of CD8αβ T cells by NKG2D via engagement by MIC induced on virus-infected cells," *Nature Immunology*, 2(3):255-260, 2001.
Groh et al., "Recognition of stress-induced MHC molecules by intestinal epithelial γδ T cells," *Science*, 279:1737-1740, 1998.
Ivashiv, "Cytokine expression and cell activation in inflammatory arthritis," *Adv Immunol*, 63:337-376, 1996.

(Continued)

Primary Examiner—Ram R Shukla
Assistant Examiner—Zachary Skelding
(74) Attorney, Agent, or Firm—Fulbright & Jaworski L.L.P.

(57) ABSTRACT

The present invention relates to methods of treating immune disorders, particularly autoimmune and inflammatory disorders such as rheumatoid arthritis, and methods of producing antibodies for use in therapeutic strategies for treating such disorders. Generally, the present methods involve the use of antibodies that specifically bind to NKG2D receptors present on the surface of cells underlying the disorders.

10 Claims, No Drawings

OTHER PUBLICATIONS

Klavins et al., "Advances in biological markers for cancer," *Ann Clin Lab Sci*, 13:275-280, 1983.

Klimiuk et al., "Production of cytokines and metalloproteinases in rheumatoid synovitis is T cell dependent," *Clin Immunol*, 90:65-78, 1999.

Krause et al., "Rheumatoid arthritis synoviocyte survival is dependent on stat3," *J. Immunol*, 169:6610-6616, 2002.

Kurowska et al., "Fibroblast-like synoviocytes from rheumatoid arthritis patients express functional IL-15 receptor complex: endogenous IL-15 in autocrine fashion enhances cell proliferation and expression of Bcl-$x_L$ and Bcl-$2_l$," *J Immunol*, 169:1760-1767, 2002.

Lanier et al., "Turning on natural killer cells," *J Exp Med*, 191(8):1259-1262, 2000.

Lanier, "On guard-activating NK cell receptors," *Nat Immunol*, 2:23-27, 2001.

Li et al., "Complex structure of the activating immunoreceptor NKG2D and its MHC class I-like ligand MICA," *Nat Immunol*, 2(5):443-451, 2001.

Martens et al., "Expansion of unusual CD4+ T cells in severe rheumatoid arthritis," *Arthritis and Rheumatism*, 40(6):1106-1114, 1997.

McInnes et al., "The role of interleukin-15 in T-cell migration and activation in rheumatoid arthritis," *Nat Med*, 2(2):175-182, 1996.

McInnes et al., "Interleukin-15 mediates T cell-dependent regulation of tumor necrosis factor-α production in rheumatoid arthritis," *Nat Med*, 3(2):189-195, 1997.

Mingari et al., "Human CD8+ T lymphocyte subsets that express HLA class I-specific inhibitory receptors represent oligoclonally or monoclonally expanded cell populations," *Proc. Natl. Acad. Sci., USA*, 93:12433-12438, 1996.

Moser et al., "CD94-NKG2A receptors regulate antiviral CD8+ T cell receptors," *Nature Immunology*, 3(2):189-195, 2002.

Muller-Ladner et al., "Molecular biology of cartilage and bone destruction," *Curr Opin Rheumatol*, 10:212, 1998.

Namekawa et al., "Functional subsets of DC4 T cells in rheumatoid synovitis," *Arthritis and Rheumatism*, 41(12):2108-2116, 1998.

Park et al., "Co-stimulatory pathways controlling activation and peripheral tolerance of human CD4'CD28- T cells," *Eur J Immunol*, 27:1082-1090, 1997.

Pohl et al., "Present value of tumor markers in clinic," *Cancer Detect Prevent*, 6:7-20, 1983.

Ravetech et al., "Immune inhibitory receptors," *Science*, 290:84-89, 2000.

Roberts et al., "Cutting edge: NKG2D receptors induced by IL-15 costimulate CD28-negative effector CTL in the tissue microenvironment," *J Immunol*, 167:5527, 2001.

Schmidt et al., "CD4+ CD7-CD28- T cells are expanded in rheumatoid arthritis and are characterized by autoreactivity," *J. Clin Invest*, 97:2027-2037, 1996.

Sikorska et al., "Clinical applications of carcinoembryonic antigen," *Cancer Detect Prevent*, 12:321-355, 1988.

Snyder et al., "Formation of the killer Ig-like receptor repertoire on CD4+CD28 null T cells," *J. Immunol*, 168:3839-3846, 2002.

Speiser et al., "CD28-negative cytolytic effector T cells frequently express NK receptors and are present at variable proportions in circulating lymphocytes from health donors and melanoma patients," *Eur J Immunol*, 29:1990-1999, 1999.

Steinle et al., "Interactions of human NKG2D with its ligands MICA, MICB and homologs of the mouse RAE-1 protein family," *Immunogenetics*, 53(4):279-287, 2001.

Sultzeanu et al., "Human and cancer associated antigens: present status and implications for immunodiagnosis," *Adv Cancer Res*, 44:1-42, 1985.

Tieng et al., "Binding of *Escherichia coli* adhesin AfaE to CD55 triggers cell-surface expression of the MHC class I-related molecule MICA," *Proc. Natl. Acad. Sci., USA*, 99(5):2977-2982, 2002.

Vallejo et al., "Clonality and longevity of CD4+CD28 null T cells are associated with defects in apoptotic pathways," *J Immunol*, 165:6301-6307, 2000.

Viriji et al., "Tumor markers in cancer diagnosis and prognosis," *Cancer*, 38:105-126, 1988.

Warrington et al., "CD4+, CD28- T cells rheumatoid arthritis patients combine features of the innate and adaptive immune systems," *Arthritis and Rheumatism*, 44:13-20, 2001.

Wu et al., "An activating immunoreceptor complex formed by NKG2D and DAP10," *Science*, 285:730-732, 1999.

Yen et al., "Major histocompatibility complex class I-recognizing receptors are disease risk genes in rheumatoid arthritis," *J Exp Med*, 193:1159-1167, 2001.

Li et al., "A single amino acid substitution causes loss of expression of a MICA allele," *Immunogenetics*, 51:246-248, 2000.

Salih et al., "Cutting Edge: Down-Regulation of MICA on Human Tumors by Proteolytic Shedding," *J. Immunol.*, 169:4098-4102, 2002.

U.S. Appl. No. 10/512,181, filed May 18, 2005, Spies et al.

Brailly, Innate Pharma Letter to Mr. Spencer Lemmons, Sep. 15, 2006.

Groh et al., "Stimulation of T cell autoreactivity by anomalous expression of NKG2D and its MIC ligands in rheumatoid arthritis," *Proc. Nat'l. Acad, Sci. USA*, 100:9452, 2003.

Spies et al., "Biology and Significance of Activating Immunoreceptors," Research Grant Proposal, Fred Hutchinson Cancer Research Center, Sep. 25, 2001.

Spies et al., "Cell-Stress Induced Immune Responses," Research Grant Proposal, Fred Hutchinson Cancer Research Center, Jun. 21, 2000.

Spies et al., "Novel Immune Response Genes within the Human MHC," Research Grant Proposal, Fred Hutchinson Cancer Research Center, Mar. 5, 1996.

Armeau et al., "Natural killer cell-mediated lysis of hepatoma cells via specific induction of NKG2D ligands by the histone deacetylase inhibitor sodium valproate," *Cancer Res.*, 65:6321-6329, 2005.

Atkinson and Letter, "The NOD mouse model of type 1 diabetes: as good as it gets?," *Nat. Med.*, 5:601-604, 1999.

Bakker et al., "DAP12-deficient mice fail to develop autoimmunity due to impaired antigen priming," *Immunity*, 13:345-353, 2000.

Baron et al., "Activation of a nonclassical NKT cell subset in a transgenic mouse model of hepatitis B virus infection," *Immunity*, 16:583-594, 2002.

Carayannopoulos et al., "Cutting edge: murine UL16-binding protein-like transcript 1: a newly described transcript encoding a high-affinity ligand for murine NKG2D," *J. Immunol.*, 169:4079-4083, 2002.

Carayannopoulos et al., "Ligands for murine NKG2D display heterogeneous binding behavior," *Eur. J. Immunol.*, 32:597-605, 2002.

Cerwenka et al., "Ectopic expression of retinoic acid early inducible-1 gene (RAE-1) permits natural killer cell-mediated rejection of a MHC class I-bearing tumor in vivo," *Proc. Natl. Acad. Sci. USA*, 98:11521-11526, 2001.

Cerwenka et al., "Retinoic acid early inducible genes define a ligand family for the activating NKG2D receptor in mice," *Immunity*, 12:721-727, 2000.

Cosman et al., "ULBPs, novel MHC class I-related molecules, bind to CMV glycoprotein UL16 and stimulate NK cytotoxicity through the NKG2D receptor," *Immunity*, 14:123-133, 2001.

Dandekar et al., "Important roles for gamma interferon and NKG2D in gammadelta T-cell-induced demyelination in T-cell receptor beta-deficient mice infected with a coronavirus," *J. Virol.*, 79:9388-9396, 2005.

Ehrlich et al., "Engagement of NKG2D by cognate ligand or antibody alone is insufficient to mediate costimulation of human and mouse CD8+ T cells," *J. Immunol.*, 174:1922-1931, 2005.

Geissmann et al., "Intravascular immune surveillance by CXCR6+ NKT cells patrolling liver sinusoids," *PLOS Biology*, 3:650-661, 2005.

Genbank Accession No. AF285448, pig NKG2D, dated Aug. 9, 2001.

Genbank Accession No. AF470403, orangutan NKG2D, dated Jul. 18, 2002.

Genbank Accession No. AJ554302, rhesus monkey NKG2D, dated Apr. 29, 2005.

Genbank Accession No. NM_007360, human NKG2D, dated Jan. 13, 2008.

Genbank Accession No. NM_033078, house mouse NKG2D, dated Dec. 23, 2007.

Genbank Accession No. NM_133512, Norway rat NKG2D, dated Sep. 25, 2007.
George et al., "Tolerance and alloreactivity of the Ly49D subset of murine NK cells," *J. Immunol.*, 163:1859-1867, 1999.
Hue et al., "A direct role for NKG2D/MICA interaction in villous atrophy during celiac disease," *Immunity*, 21:367-377, 2004.
Jamieson et al., "The role of the NKG2D immunoreceptor in immune cell activation and natural killing," *Immunity*, 17:19-29, 2002.
Jinushi et al., "Autocrine/paracrine IL-15 that is required for type I IFN-mediated dendritic cell expression of MHC class I-related chain A and B is impaired in hepatitis C virus infection," *J. Immunol.*, 171:5423-5429, 2003.
Jinushi et al., "Critical role of MHC class I-related chain A and B expression on IFN-alpha-stimulated dendritic cells in NK cell activation: impairment in chronic hepatitis C virus infection," *J. Immunol.*, 170:1249-1256, 2003.
Jinushi et al., "Expression and role of MICA and MICB in human hepatocellular carcinomas and their regulation by retinoic acid," *Int. J. Cancer*, 104:354-361, 2003.
Kakimi et al., "Natural killer T cell activation inhibits hepatitis B virus replication in vivo," *J. Exp. Med.*, 192:921-930, 2000.
Kiessling et al., "Evidence for a similar or common mechanism for natural killer cell activity and resistance to hemopoietic grafts," *Eur. J. Immunol.*, 7:655-663, 1977.
Lodoen et al., "NKG2D-mediated natural killer cell protection against cytomegalovirus is impaired by viral gp40 modulation of retinoic acid early inducible 1 gene molecules," *J. Exp. Med.*, 197:1245-1253, 2003.
Lodoen et al., "The cytomegalovirus m155 gene product subverts natural killer cell antiviral protection by disruption of H60-NKG2D interactions," *J. Exp. Med.*, 200:1075-1081, 2004.
Lotzova et al., "Prevention of rejection of allogeneic bone marrow transplants by NK 1.1 antiserum," *Transplantation*, 35:490-494, 1983.
Maier et al., "Inhibition of natural killer cells results in acceptance of cardiac allografts in CD28-/- mice," *Nat. Med.*, 7:557-562, 2001.
Malarkannan et al., "The molecular and functional characterization of a dominant minor H antigen, H60," *J. Immunol.*, 161:3501-3509, 1998.
McNerney et al., "Role of natural killer cell subsets in cardiac allograft rejection," *Am. J. Transplant.*, 6:505-513, 2006.
Meresse et al., "Coordinated induction by IL15 of a TCR-independent NKG2D signaling pathway converts CTL into lymphokine-activated killer cells in celiac disease," *Immunity*, 21:357-366, 2004.
Murphy et al., "Acute rejection of murine bone marrow allografts by natural killer cells and T cells. Differences in kinetics and target antigens recognized," *J. Exp. Med.*, 166:1499-1509, 1987.
Murphy et al., "Natural killer cells activated with interleukin 2 in vitro can be adoptively transferred and mediate hematopoietic histocompatibility-1 antigen-specific bone marrow rejection in vivo," *Eur. J. Immunol.*, 20:1729-1734, 1990.
Murphy et al., "Rejection of bone marrow allografts by mice with severe combined immune deficiency (SCID). Evidence that natural killer cells can mediate the specificity of marrow graft rejection," *J. Exp. Med.*, 165:1212-1217, 1987.
Nowbakht et al., "Ligands for natural killer cell-activating receptors are expressed upon the maturation of normal myelomonocytic cells but at low levels in acute myeloid leukemias," *Blood*, 105:3615-3622, 2005.
O'Callaghan et al., "Molecular Competition for NKG2D: H60 and RAE1 Compete Unequally for NKG2D with Dominance of H60," *Immunity*, 15:201-211, 2001.

Ogasawara et al., "A role for NKG2D in NK cell-mediated rejection of mouse bone marrow grafts," *Nat. Immunol.*, 6:938-945, 2005.
Ogasawara et al., "Impairment of NK cell function by NKG2D modulation in NOD mice," *Immunity*, 18:41-51, 2003.
Ogasawara et al., "Inducible costimulator costimulates cytotoxic activity and IFN-gamma production in activated murine NK cells," *J. Immunol.*, 169:3676-3685, 2002.
Ogasawara et al., "NKG2D blockade prevents autoimmune diabetes in NOD mice," *Immunity*, 20:757-767, 2004.
Park et al., "MICA polymorphism is associated with type 1 diabetes in the Korean population," *Diabetes Care*, 24:33-38, 2001.
Raulet, "Roles of the NKG2D immunoreceptor and its ligands," *Nat. Rev. Immunol.*, 3:781-790, 2003.
Sollid, "Intraepithelial lymphocytes in celiac disease: license to kill revealed," *Immunity*, 21:303-304, 2004.
Sutherland et al., "The UL16-binding proteins, a novel family of MHC class I-related ligands for NKG2D, activate natural killer cell functions," *Immunol. Rev.*, 181:185-192, 2001.
Sutherland et al., "UL16-binding proteins, novel MHC class I-related proteins, bind to NKG2D and activate multiple signaling pathways in primary NK cells," *J. Immunol.*, 168:671-679, 2002.
Takeda et al., "Critical contribution of liver natural killer T cells to a murine model of hepatitis," *Proc. Natl. Acad. Sci. USA*, 97:5498-5503, 2000.
Verdaguer et al., "Spontaneous autoimmune diabetes in monoclonal T cell nonobese diabetic mice," *J. Exp. Med.*, 186:1663-1676, 1997.
Zhang et al., "The inhibitory effects of synthetic short peptides, mimicking MICA and targeting at NKG2D receptors, on function of NK cells," *Peptides*, 26:405-412, 2005.
Allez et al., "CD4+NKG2D+ T Cells in Crohn's Disease Mediate Inflammatory and Cytotoxic Responses Through MICA Interactions," *Gastroenterology*, 132:2346-2358, 2007.
Caillat-Zucman, "How NKG2D ligands trigger autoimmunity?," *Human Immunology*, 67:204-207, 2006.
Coudert and Held, "The role of the NKG2D receptor for tumor immunity," *Seminars in Cancer Biology*, 16:333-343, 2006.
Deng and Mariuzza, "Structural basis for recognition of MHC and MHC-like ligands by natural killer cell receptors," *Seminars in Immunol.*, 18:159-166, 2006.
Goronzy et al., "Costimulatory pathways in rheumatoid synovitis and T-cell senescence," *Ann. N.Y. Acad. Sci.*, 1062:182-194, 2005.
Kjellev et al., "Inhibition of NKG2D receptor function by antibody therapy attenuates transfer-induced colitis in SCID mice," *Eur. J. Immunol.*, 37:1397-1406, 2007.
Lanier, "NK cell recognition," *Annu. Rev. Immunol.*, 23:225-274, 2005.
Ogasawara and Lanier, "NKG2D in NK and T cell-mediated immunity," *J. Clin. Immunol.*, 25:534-540, 2005.
Perera et al., "Expression of nonclassical class I molecules by intestinal epithelial cells," *Inflamm. Bowel Dis.*, 13:298-307, 2007.
Saikali et al., "NKG2D-mediated cytotoxicity toward oligodendrocytes suggests a mechanism for tissue injury in multiple sclerosis," *J. Neurosci.*, 27(5):1220-1228, 2007.
Stephens, "MICA and MICB genes: can the enigma of their polymorphism be resolved?," *Trends in Immunology*, 22:378-385, 2001.
Doubrovina et al., "Evasion from NK cell immunity by MHC class I chain-related molecules expressing colon adenocarcinoma," *The Journal of Immunology*, 171:6891-6899, 2003.

\* cited by examiner

METHODS AND COMPOSITIONS FOR TREATING AUTOIMMUNE DISEASES OR CONDITIONS

The present application is a continuation-in-part application claiming the benefit of priority to PCT US03/12299 filed on Apr. 22, 2003, which is hereby incorporated by reference.

This invention was made with government support under grant number AI030581 awarded by the National Institutes of Health. The government has certain rights in the invention.

FIELD OF THE INVENTION

The present invention relates to methods of treating immune disorders, particularly autoimmune and inflammatory disorders such as rheumatoid arthritis, and methods of producing antibodies and other compounds for use in therapeutic strategies for treating such disorders. Generally, the present methods involve the use of antibodies or other compounds that prevent the activation of NKG2D receptors on cells that contribute to the pathology of the disorders.

BACKGROUND

Maintaining effective immune surveillance without provoking autoimmune reactions requires the precise titration of effector T cell responses. This fine-tuning may involve the integration of negative or positive signals transduced by inhibitory or activating isoforms, such as the different killer cell Ig-like receptors (KIR), which interact with MHC class I HLA-A, -B, or -C alleles, and the inhibitory CD94-NKG2A and activating CD94-NKG2C heterodimers, which interact with HLA-E. Some of these receptors have the capacity to modulate thresholds of T cell antigen receptor-dependent T cell activation. In the rare absence of inhibitory receptors, the activating isoforms may augment T cell effector functions and contribute to autoimmune pathology.

NKG2D is an activating receptor that interacts with the MHC class I-related MICA and MICB glycoproteins, among other ligands. MICA and MICB have no role in antigen presentation, are generally only found in intestinal epithelium, and can be stress-induced in permissive types of cells by viral and bacterial infections, malignant transformation, and proliferation. NKG2D is a C-type lectin-like activating receptor that signals through the associated DAP10 adaptor protein, which is similar to CD28. It is expressed on most natural killer (NK) cells, CD8 T cells, and T cells, but not, in general, on CD4 T cells. Ligand engagement of NKG2D activates NK cells and potently co-stimulates effector T cells. However, expression of NKG2D is controlled by ligand-induced down-modulation, which is transient and rapidly reversed in the presence of IL-15. Because ligand binding unconditionally triggers NKG2D, its dysregulation together with anomalous expression of MIC in local tissue environments could promote autoreactive T cell stimulation. Other NKG2D ligands include ULBP proteins, e.g., ULBP-1, -2, and -3, originally identified as ligands for the human cytomegalovirus glycoprotein UL16. These proteins are distantly related to MHC class I proteins, but they possess only the a1 and a2 Ig-like domains, and they have no capacity to bind peptide or interact with b2-microglobulin.

Rheumatoid arthritis involves lymphocyte infiltrates, inflammatory mediators, and synovial hyperplasia resulting from aggressive proliferation of fibroblast-like synoviocytes and macrophages. Prognoses of joint erosions and disease severity correlate with high frequencies of clonally expanded $CD4^+CD28^-$ T cells, which are rare in healthy individuals but occur in other autoimmune disorders. These T cells can be cytotoxic, secrete large amounts of IFN-gamma, and proliferate upon stimulation with autologous adherent mononuclear cells.

Monoclonal antibody-based therapies are now available or in clinical trials for certain diseases, particularly cancers such as non-Hodgkins's lymphoma and breast cancer. The antibodies used in such therapies are generally derived from a non-human animal, and then "humanized" or "chimerized" in order to make them suitable for use in humans. Some monoclonal antibodies are used alone, such as Rituxan (for treatment of non-Hodgkin's lymphoma), Herceptin (for treatment of breast cancer), Campath (for treatment of B-CLL), where they can either slow down or stop the growth of the targeted cells, inhibit their activity, trigger apoptosis, or mark them for destruction by the immune system. In contrast, other antibodies are coupled to toxic moieties, such as radioisotopes, so that they directly kill the targeted cells simply by binding to the targeted receptors. Examples of such antibodies include Zevalin, Bexxar, and Oncolym (all for treatment of non-Hodgkin's lymphoma).

SUMMARY OF THE INVENTION

The present invention provides methods for producing antibodies and other compounds useful in the treatment of autoimmune and inflammatory disorders such as rheumatoid arthritis (RA). The antibodies and compounds produced using the present methods are capable of specifically targeting and/or inhibiting the NKG2D receptor on immune cells such as T cells, e.g., $CD4^+$ T cells, in patients. The antibodies and compounds can limit the pathological effects of cells expressing the NKG2D receptor, e.g., by interfering with the activation of the cells, or, alternatively, by killing them directly by contacting them with a cytotoxic agent such as a radioisotope, toxin, or drug. Methods of using the antibodies and compounds for the treatment of any of a number of autoimmune or inflammatory disorders are also provided, as are kits comprising the herein-described antibodies and/or compounds as well as instructions for their use.

Accordingly, the present invention provides a method of treating a patient with an inflammatory or autoimmune disorder, the method comprising administering to the patient a pharmaceutical composition comprising an inhibitor of an NKG2D receptor, and a pharmaceutically acceptable carrier.

In one embodiment, the inhibitor is a monoclonal antibody, or a fragment or derivative thereof. In another embodiment, the antibody is humanized, chimeric, or human. In another embodiment, the antibody is derived from a monoclonal antibody selected from the group consisting of 1D11, BAT221, ECM217, and ON72. In another embodiment, the inhibitor interferes with the binding of an NKG2D ligand to the NKG2D receptor. In another embodiment, the inflammatory or autoimmune disorder is rheumatoid arthritis. In another embodiment, the inflammatory or autoimmune disorder is selected from the group consisting of Wegener's granulomatosis, Sjogren's syndrome, and insulin-dependent diabetes mellitus.

In another embodiment, the method further comprises the administration of a pharmaceutical composition comprising a therapeutic compound selected from the group consisting of an inhibitor of TNF-alpha, an inhibitor of IL-15, an inhibitor of MICA, an inhibitor of MICB, an inhibitor of ULBP-1, an inhibitor of ULBP-2, an inhibitor of ULBP-3, and IL-10. In another embodiment, the patient has an elevated level of NKG2D-expressing T cells. In another embodiment, the T cells are CD4$^+$. In another embodiment, the T cells are CD28$^-$.

In another embodiment, the method further comprises a diagnostic step in which, prior to the administration of the inhibitor, the prevalence of NKG2D-expressing CD4$^+$ T cells in the patient is assessed, wherein a detection of elevated levels of such cells in the patient indicates that the patient is suitable for the administration of the inhibitor. In another embodiment, the CD4$^+$ T cells are CD4$^+$CD28$^-$. In another embodiment, the diagnostic step comprises an immunoassay to detect the presence of CD4, CD28, or NKG2D on T cells obtained from the patient.

In another embodiment, the antibody is a cytotoxic antibody. In another embodiment, the cytotoxic antibody comprises an element selected from the group consisting of radioactive isotope, toxic peptide, and toxic small molecule.

In another aspect, the present invention provides a method of producing an antibody or other compound suitable for use in the treatment of an autoimmune or inflammatory disorder, said method comprising the following steps: a) providing a NKG2D receptor-expressing CD4$^+$CD28$^-$ T cell and a plurality of monoclonal antibodies or other compounds; b) testing the ability of each of the antibodies or compounds to interfere with the binding of a ligand to the NKG2D receptor on said cells; c) selecting an antibody or compound from the plurality that reduces the binding of the ligand to the receptor; and d) if an antibody is selected in step c), rendering the antibody suitable for human administration.

In one embodiment, the antibody is made suitable for human administration by humanizing or chimerizing it. In another embodiment, the method further comprises a step in which a cytotoxic agent is linked to the antibody. In another embodiment, the cytotoxic agent is a radioactive isotope, a toxic polypeptide, or a toxic small molecule.

In another embodiment, the antibody or compound reduces the binding of the ligand to the receptor by at least a percentage selected from the group consisting of 50%, 60%, 70%, 80%, 90%, 95%, and 99%. In another embodiment, the autoimmune or inflammatory disorder is rheumatoid arthritis. In another embodiment, the autoimmune or inflammatory disorder is selected from the group consisting of Wegener's granulomatosis, Sjogren's syndrome, and insulin-dependent diabetes mellitus. In another embodiment, the ligand is selected from the group consisting of MICA, MICB, ULBP-1, ULBP-2, and ULBP-3. In another embodiment, the antibody is derived from a monoclonal antibody selected from the group consisting of 1D11, BAT221, ECM217, and ON72.

In another embodiment, the method further comprises a step in which the activity of the NKG2D receptor on the T cells is assessed in the presence of the ligand and the antibody or compound. In another embodiment, the activity is assessed using an assay selected from the group consisting of cytotoxicity assays, cytokine release assays, gene expression assays, and proliferation assays.

In another aspect, the present invention provides antibodies or compounds produced using any of the herein-described methods. The invention also encompasses fragments and derivatives of the antibodies having substantially the same antigen specificity and activity (e.g., which can bind to the same antigens as the parent antibody). Such fragments include, without limitation, Fab fragments, Fab'2 fragments, CDR and ScFv.

In another aspect, the present invention provides kits comprising any one or more of the herein-described antibodies or compounds. Typically, the kit also comprises instructions for using the antibodies according to the present methods.

The invention also comprises pharmaceutical compositions comprising one or more of the present antibodies, or a fragment or derivative thereof, or any of the present compounds, and a pharmaceutically acceptable carrier or excipient.

DETAILED DESCRIPTION OF THE INVENTION

Introduction

The present invention provides novel methods for producing and using antibodies and other compounds suitable for the treatment of autoimmune and inflammatory disorders such as rheumatoid arthritis. Antibodies, antibody derivatives, or antibody fragments produced using the herein described methods are encompassed, as are methods of treating patients using the antibodies and compounds.

The present invention is based, in part, on the surprising discovery that rheumatoid arthritis and other immunoproliferative disorders are often associated with abnormal expression of the NKG2D receptor in immune cells, particularly CD4$^+$ cells, and most particularly CD4$^+$CD28$^-$ T cells. The present invention thus provides a method of treating such disorders by, optionally, first detecting the prevalence of cells expressing CD4, CD28, NKG2D, and/or NKG2D ligands such as MICA, MICB, or a ULBP protein, in a patient (either systemically or locally), and then administering one or more antibodies or other compounds that can inhibit the activity of or otherwise target the NKG2D receptor. In this way, the function of the cells is inhibited by, e.g., blocking activation of the receptor, or, alternatively, by killing the cells using cytotoxic antibodies directed against NKG2D. PCT US03/12299 Application filed on Apr. 22, 2003 is hereby incorporated by reference in its entirety.

Definitions

As used herein, the following terms have the meanings ascribed to them unless specified otherwise.

As used herein, "T" cells refers to a sub-population of lymphocytes that mature in the thymus, and which display, among other molecules T cell receptors on their surface. T cells can be identified by virtue of certain characteristics and biological properties, such as the expression of specific surface antigens including the TCR, CD4 or CD8, the ability of certain T cells to kill tumor or infected cells, the ability of certain T cells to activate other cells of the immune system, and the ability to release protein molecules called cytokines that stimulate or inhibit the immune response. Any of these characteristics and activities can be used to identify T cells, using methods well known in the art.

The term "NKG2D" refers to an activating cell surface molecule that is found consistently on all or a fraction of numerous types of immune cells, particularly NK cells, CD8$^+$ T cells, some CD4$^+$ T cells, and gamma/delta T cells. NKG2D is also referred to as killer cell lectin-like receptor, subfamily C, member 4, or as KLRC4 (see, e.g., OMIM 602893, the entire disclosure of which is herein incorporated by reference in its entirety.) As used herein NKG2D refers to any NKG2D isoform, e.g., the isoforms described in Diefenbach et al. (2002) Nat Immunol. 3(12):1142-9). In NK and T cells, NKG2D can form heterodimers with proteins such as DAP10 (see, e.g., OMIM 604089) or DAP12 (see, e.g., OMIM 604142). It will be appreciated that any activity attributed herein to NKG2D, e.g., cell activation, recognition by antibodies, etc., can also refer to NKG2D-including complexes such as NKG2D-DAP10 or NKG2D-DAP12 heterodimers.

"Autoimmune" disorders include any disorder, condition, or disease in which the immune system mounts a reaction against self cells or tissues, due to a breakdown in the ability to distinguish self from non-self or otherwise. Examples of autoimmune disorders include Hashimoto's thyroiditis, pernicious anemia, Addison's disease, type I diabetes, rheumatoid arthritis, systemic lupus erythematosus, dermatomyositis, Sjogren's syndrome, lupus erythematosus, multiple sclerosis, myasthenia gravis, Reiter's syndrome, Grave's disease, polymyositis, Guillain Barre, Wegener's granulomatosus, polyarteritis nodosa, polymyalgia rheumatica, temporal arteritis, Bechet's disease, Churg-Strauss syndrome, Takayasu's arteritis, and others. Autoimmune disorders can involve any component of the immune system, and can target any cell or tissue type in the body.

"Inflammatory diseases" refer to any disorder, condition, or disease characterized or caused by excessive or uncontrolled inflammation, or any aspect of inflammation such as redness, swelling, heat, pain, etc. Inflammatory diseases include allergies, including allergic rhinitis/sinusitis, skin allergies such as urticaria/hives, angioedema, atopic dermatitis, food allergies, drug allergies, insect allergies, and rare allergic disorders such as mastocytosisasthma, asthma, arthritis, including osteoarthritis, rheumatoid arthritis, and spondyloarthropathies, gastrointestinal inflammation, neuroinflammatory disorders, and autoimmune disorders.

As used herein, the term rheumatoid arthritis refers to any disorder involving inflammation of the joints, and including features such as joint erosion, lymphocyte infiltration, synovial hyperplasia, aggressive proliferation of fibroblast-like synoviocytes and macrophages, and/or the presence of $CD4^+$ $NKG2D^+$ cells.

The terms "inhibiting," "downmodulating," and "downregulating," with respect to NKG2D or NKG2D-expressing cells means a process, method, or compound that can slow down, reduce, reverse, or in any way negatively affect the activity or number of NKG2D receptors or cells expressing NKG2D. These terms can refer to compounds that inhibit the activation of NKG2D by a ligand, that act antagonistically in the absence of a ligand to decrease the activity of the receptor, that decrease the expression level of the receptor, that block NKG2D-triggered signaling or gene expression, or that block any other activity of the cell that results from NKG2D activation. In a preferred embodiment, the inhibiting compound or method targets the binding of the receptor by a ligand, e.g. by binding to the receptor and preventing ligand access. The number of NKG2D receptor molecules or any of the herein-described activities can be measured in any standard way, e.g. as disclosed elsewhere in the present application.

The term "antibody," as used herein, refers to polyclonal and monoclonal antibodies. Depending on the type of constant domain in the heavy chains, antibodies are assigned to one of five major classes:IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed in this invention, with IgG being particularly preferred, because they are the most common antibodies in the physiological situation and because they are most easily made in a laboratory setting. Preferably the antibody of this invention is a monoclonal antibody. Particularly preferred are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. NKG2D, as assessed using either recombinant forms of the proteins, epitopes therein, or native proteins present on the surface of isolated T or NK or other target cells. Competitive binding assays and other methods for determining specific binding are further described below and are well known in the art.

A "human-suitable" antibody refers to any antibody, derivatized antibody, or antibody fragment that can be safely used in humans for, e.g. the therapeutic methods described herein. Human-suitable antibodies include all types of humanized, chimeric, or fully human antibodies, or any antibodies in which at least a portion of the antibodies is derived from humans or otherwise modified so as to avoid the immune response that is generally provoked when native non-human antibodies are used.

"Toxic" or "cytotoxic" peptides or small molecules encompass any compound that can slow down, halt, or reverse the proliferation of cells, decrease their activity in any detectable way, or directly or indirectly kill them. Preferably, toxic or cytotoxic compounds work by directly killing the cells, by provoking apoptosis or otherwise. As used herein, a toxic "peptide" can include any peptide, polypeptide, or derivative of such, including peptide- or polypeptide-derivatives with unnatural amino acids or modified linkages. A toxic "small molecule" can includes any toxic compound or element, preferably with a size of less than 10 kD, 5 kD, 1 kD, 750 D, 600 D, 500 D, 400 D, 300 D, or smaller.

By "immunogenic fragment", it is herein meant any polypeptidic or peptidic fragment that is capable of eliciting an immune response such as (i) the generation of antibodies binding said fragment and/or binding any form of the molecule comprising said fragment, including the membrane-bound receptor and mutants derived therefrom, (ii) the stimulation of a T-cell response involving T-cells reacting to the bi-molecular complex comprising any MHC molecule and a peptide derived from said fragment, (iii) the binding of transfected vehicles such as bacteriophages or bacteria expressing genes encoding mammalian immunoglobulins. Alternatively, an immunogenic fragment also refers to any construction capable of eliciting an immune response as defined above, such as a peptidic fragment conjugated to a carrier protein by covalent coupling, a chimeric recombinant polypeptide construct comprising said peptidic fragment in its amino acid sequence, and specifically includes cells transfected with a cDNA of which sequence comprises a portion encoding said fragment.

For the purposes of the present invention, a "humanized" antibody refers to an antibody in which the constant and variable framework region of one or more human immunoglobulins is fused with the binding region, e.g. the CDR, of an animal immunoglobulin. Such humanized antibodies are designed to maintain the binding specificity of the non-human antibody from which the binding regions are derived, but to avoid an immune reaction against the non-human antibody.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "human" antibody is an antibody obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

Within the context of this invention, "active" or "activated" T cells designate biologically active T cells, more particularly T cells having the capacity of cytolysis or of stimulating an immune response by, e.g., secreting cytokines. For instance, an "active" $CD4^+$ $NKG2D^+$ T cell is able to stimulate the killing of MICA or MICB producing cells, e.g. proliferating synoviocytes in RA. Active cells can be detected in any of a number of well known methods, including functional assays and expression-based assays such as the expression of cytokines such as TNF-alpha.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The term "biological sample" as used herein includes but is not limited to a biological fluid (for example serum, lymph, blood), cell sample or tissue sample (for example bone marrow).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Producing Monoclonal Antibodies Specific for NKG2D

The present invention involves the production and use of antibodies and other molecules that are capable of inhibiting NKG2D activation on immune cells such as T cells. The antibodies of this invention may be produced by any of a variety of techniques known in the art. Typically, they are produced by immunization of a non-human animal, preferably a mouse, with an immunogen comprising an NKG2D receptor on the surface of cells such as T cells or NK cells. The receptor may comprise entire cells or cell membranes, the full length sequence of an NKG2D, or a fragment or derivative of any NKG2D, typically an immunogenic fragment, i.e., a portion of the polypeptide comprising an epitope exposed on the surface of cells expressing the receptor. Any isoform or splicing fragment of NKG2D can be used (see, e.g., OMIM 602893 or Diefenbach et al. (2002) *Nature Immun.* 3:1142-1149; the disclosures of which are herein incorporated by reference). Such fragments typically contain at least 7 consecutive amino acids of the mature polypeptide sequence, even more preferably at least 10 consecutive amino acids thereof. They are essentially derived from the extracellular domain of the receptor. In preferred embodiments, the NKG2D receptor used to generate antibodies is a human receptor. In certain embodiments, NKG2D present in a heterodimer, e.g. in association with DAP10 or DAP12, can be used to generate antibodies.

In a most preferred embodiment, the immunogen comprises a wild-type human NKG2D receptor polypeptide in a lipid membrane, typically at the surface of a cell. In a specific embodiment, the immunogen comprises intact NK or T cells, particularly intact human NK or T cells, optionally treated or lysed. In a preferred embodiment, the immunogen is a CD4+, preferably a $CD4^+CD28^-$, T cell taken from a patient with rheumatoid arthritis or other autoimmune or inflammatory disorder.

In one embodiment, the antibodies are derived from one or more already-existing monoclonal antibodies that recognize NKG2D, e.g. 1D11, BAT221, ECM217, and ON72 (see, e.g. Groh et al. (2003) PNAS 100:9452-57; André et al. (2004) Eur. J. Immunol. 34:1-11; the entire disclosures of which are herein incorporated by reference). For certain applications, such antibodies can be directly or indirectly labeled (i.e., used with a labeled secondary antibody) for use as diagnostic antibodies to determine the presence of NKG2D on the presence of cells, preferably $CD4^+CD28^-$ cells from patient with RA or other disorders. In addition, the antibodies can be made suitable for human administration and, optionally, made toxic as described herein for use as cytotoxic antibodies in the present therapeutic methods.

The present diagnostic or therapeutic (e.g. cytotoxic) antibodies can be full length antibodies or antibody fragments or derivatives. Examples of antibody fragments include Fab, Fab', Fab'-SH, $F(ab')_2$, and Fv fragments; diabodies; single-chain Fv (scFv) molecules; single chain polypeptides containing only one light chain variable domain, or a fragment thereof that contains the three CDRs of the light chain variable domain, without an associated heavy chain moiety; single chain polypeptides containing only one heavy chain variable region, or a fragment thereof containing the three CDRs of the heavy chain variable region, without an associated light chain moiety; and multispecific antibodies formed from antibody fragments. Such fragments and derivatives and methods of preparing them are well known in the art. For example, pepsin can be used to digest an antibody below the disulfide linkages in the hinge region to produce $F(ab)'_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993)). While various antibody fragments are defined in terms of the digestion of an intact antibody, one of skill will appreciate that such fragments may be synthesized de novo either chemically or by using recombinant DNA methodology.

The preparation of monoclonal or polyclonal antibodies is well known in the art, and any of a large number of available techniques can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy (1985)). Techniques for the production of single chain antibodies (U.S. Pat. No. 4,946,778) can be adapted to produce antibodies to desired polypeptides, e.g., NKG2D. Also, transgenic mice, or other organisms such as other mammals, may be used to express humanized, chimeric, or similarly-modified antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). In one embodiment, the method comprises selecting, from a library or repertoire, a monoclonal antibody or a fragment or derivative thereof that cross reacts with an NKG2D receptor polypeptide. For example, the repertoire may be any (recombinant) repertoire of antibodies or fragments thereof, optionally displayed by any suitable structure (e.g., phage, bacteria, synthetic complex, etc.).

The step of immunizing a non-human mammal with an antigen may be carried out in any manner well known in the art for (see, for example, E. Harlow and D. Lane, Antibodies:A Laboratory Manual., Cold Spring Harbor Laboratory Press, Cold Spring Harbor, N.Y. (1988)). Generally, the immunogen is suspended or dissolved in a buffer, optionally with an adjuvant, such as complete Freund's adjuvant. Methods for determining the amount of immunogen, types of buffers and amounts of adjuvant are well known to those of skill in the art and are not limiting in any way on the present invention.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be utilized as long as they result in the production of B cells expressing an antibody directed to the antigen used in immunization.

In another embodiment, lymphocytes from an unimmunized non-human mammal are isolated, grown in vitro, and then exposed to the immunogen in cell culture. The lymphocytes are then harvested and the fusion step described below is carried out.

For monoclonal antibodies, which are preferred for the purposes of the present invention, the next step is the isolation of cells, e.g., lymphocytes, splenocytes, or B cells, from the immunized non-human mammal and the subsequent fusion of those splenocytes, or B cells, or lymphocytes, with an immortalized cell in order to form an antibody-producing hybridoma. Accordingly, the term "preparing antibodies from an immunized animal," as used herein, includes obtaining B-cells/splenocytes/lymphocytes from an immunized animal and using those cells to produce a hybridoma that expresses antibodies, as well as obtaining antibodies directly from the serum of an immunized animal. The isolation of splenocytes, e.g., from a non-human mammal is well-known in the art and, e.g., involves removing the spleen from an anesthetized non-human mammal, cutting it into small pieces and squeezing the splenocytes from the splenic capsule and through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the antibody-producing cells are fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, Calif. U.S.A., X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

The hybridomas can be grown on a feeder layer of macrophages. The macrophages are preferably from littermates of the non-human mammal used to isolate splenocytes and are typically primed with incomplete Freund's adjuvant or the like several days before plating the hybridomas. Fusion methods are described, e.g., in (Goding, "Monoclonal Antibodies: Principles and Practice," pp. 59-103 (Academic Press, 1986)), the disclosure of which is herein incorporated by reference.

The cells are allowed to grow in the selection media for sufficient time for colony formation and antibody production. This is usually between 7 and 14 days. The hybridoma colonies are then assayed for the production of antibodies that specifically recognize the desired substrate, e.g. NKG2D. The assay is typically a colorimetric ELISA-type assay, although any assay may be employed that can be adapted to the wells in which the hybridomas are grown. Other assays include immunoprecipitation and radioimmunoassay. The wells positive for the desired antibody production are examined to determine if one or more distinct colonies are present. If more than one colony is present, the cells may be re-cloned and grown to ensure that only a single cell has given rise to the colony producing the desired antibody. Positive wells with a single apparent colony are typically recloned and re-assayed to ensure that only one monoclonal antibody is being detected and produced.

Hybridomas that are confirmed to be producing a monoclonal antibody of this invention are then grown up in larger amounts in an appropriate medium, such as DMEM or RPMI- 1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Amersham Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

In preferred embodiments, the DNA encoding an antibody that binds a determinant present on the NKG2D immunogen is isolated from the hybridoma and placed in an appropriate expression vector for transfection into an appropriate host. The host is then used for the recombinant production of the antibody, variants thereof, active fragments thereof, or humanized or chimeric antibodies comprising the antigen recognition portion of the antibody. Preferably, the DNA used in this embodiment encodes an antibody that recognizes a determinant present on NKG2D receptors on T cells, such as $CD4^+$, e.g., $CD4^+CD28^-$, T cells taken from patient with rheumatoid arthritis or another autoimmune or inflammatory disorder.

DNA encoding the monoclonal antibodies of the invention can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant expression in bacteria of DNA encoding the antibody is well known in the art (see, for example, Skerra et al. (1993) Curr. Op. Immunol. 5:256; and Pluckthun (1992) Immunol. Revs. 130:151). Antibodies may also be produced by selection of combinatorial libraries of immunoglobulins, as disclosed for instance in Ward et al. (1989) Nature 341:544.

In a specific embodiment, the antibody binds essentially the same epitope or determinant as one of the monoclonal antibodies CX5 (Ebioscience catalog number 14-5882), 1D11, BAT221, ECM217, and ON72 (see, e.g. Groh et al. (2003) PNAS 100:9452-57; André et al. (2004) Eur. J. Immunol. 34:1-11; the entire disclosures of which are herein incorporated by reference). The term "binds to substantially the same epitope or determinant as" the monoclonal antibody x means that an antibody "can compete" with x, where x is ON72, etc. The identification of one or more antibodies that bind(s) to substantially the same epitope as the monoclonal antibody in question can be readily determined using any one of variety of immunological screening assays in which antibody competition can be assessed. Such assays are routine in the art (see, e.g., U.S. Pat. No. 5,660,827, which is herein incorporated by reference). It will be understood that actually determining the epitope to which the antibody binds is not in any way required to identify an antibody that binds to the same or substantially the same epitope as the monoclonal antibody in question.

For example, where the test antibodies to be examined are obtained from different source animals, or are even of a different Ig isotype, a simple competition assay may be employed in which the control (e.g. ON72) and test antibodies are admixed (or pre-adsorbed) and applied to a sample containing the epitope-containing protein, e.g. NKG2D in the case of ON72. Protocols based upon ELISAs, radioimmunoassays, Western blotting and the use of BIACORE (as described, e.g., in the examples section) are suitable for use in such simple competition studies and are well known in the art.

In certain embodiments, one would pre-mix the control antibodies (e.g. ON72) with varying amounts of the test antibodies (e.g., 1:10 or 1:100) for a period of time prior to applying to the antigen (e.g. NKG2D epitope) containing sample. In other embodiments, the control and varying amounts of test antibodies can simply be admixed during exposure to the antigen sample. As long as one can distinguish bound from free antibodies (e.g., by using separation or washing techniques to eliminate unbound antibodies) and the control antibody from the test antibodies (e.g., by using species- or isotype-specific secondary antibodies or by specifically labeling the control antibody with a detectable label) one will be able to determine if the test antibodies reduce the binding of the control antibody to the antigen, indicating that the test antibody recognizes substantially the same epitope as the control. The binding of the (labeled) control antibodies in the absence of a completely irrelevant antibody would be the control high value. The control low value would be obtained by incubating the labeled control antibodies (e.g. ON72) with unlabeled antibodies of exactly the same type (e.g. ON72), where competition would occur and reduce binding of the labeled antibodies. In a test assay, a significant reduction in labeled antibody reactivity in the presence of a test antibody is indicative of a test antibody that recognizes the same epitope, i.e., one that "cross-reacts" with the labeled control antibody. Any test antibody that reduces the binding of the labeled control to each the antigen by at least 50% or more preferably 70%, at any ratio of control:test antibody between about 1:10 and about 1:100 is considered to be an antibody that binds to substantially the same epitope or determinant as the control. Preferably, such test antibody will reduce the binding of the control to the antigen by at least 90%.

In one embodiment, competition can be assessed by a flow cytometry test. Cells bearing a given activating receptor are incubated first with a control antibody that is known to specifically bind to the receptor (e.g., T or NK cells expressing NKG2D, and the ON72 antibody), and then with the test antibody that has been labeled with, e.g., a fluorochrome or biotin. The test antibody is said to compete with the control if the binding obtained with preincubation with saturating amounts of control antibody is 80%, preferably, 50, 40 or less of the binding (mean of fluorescence) obtained by the antibody without preincubation with the control. Alternatively, a test antibody is said to compete with the control if the binding obtained with a labeled control (by a fluorochrome or biotin) on cells preincubated with saturating amount of antibody to test is 80%, preferably 50%, 40%, or less of the binding obtained without preincubation with the antibody.

In one preferred example, a simple competition assay may be employed in which a test antibody is pre-adsorbed and applied at saturating concentration to a surface onto which is immobilized the substrate for the antibody binding, e.g. the NKG2D protein, or epitope-containing portion thereof, which is known to be bound by ON72. The surface is preferably a BIACORE chip. The control antibody (e.g. ON72) is then brought into contact with the surface at a substrate-saturating concentration and the substrate surface binding of the control antibody is measured. This binding of the control antibody is compared with the binding of the control antibody to the substrate-containing surface in the absence of test antibody. In a test assay, a significant reduction in binding of the substrate-containing surface by the control antibody in the presence of a test antibody is indicative of a test antibody that recognizes the same epitope, i.e., one that "cross-reacts" with the control antibody. Any test antibody that reduces the binding of the control antibody to the antigen-containing substrate by at least 30% or more preferably 40% is considered to be an antibody that binds to substantially the same epitope or determinant as the control antibody. Preferably, such test antibody will reduce the binding of the control antibody to the substrate by at least 50%. It will be appreciated that the order of control and test antibodies can be reversed, that is the control antibody is first bound to the surface and the test antibody is brought into contact with the surface thereafter. Preferably, the antibody having higher affinity for the substrate antigens is bound to the substrate-containing surface first since it will be expected that the decrease in binding seen for the second antibody (assuming the antibodies are cross-reacting) will be of greater magnitude. Further examples of such assays are provided in the Examples and in Saunal et al. (1995) J. Immunol. Meth 183: 33-41, the disclosure of which is incorporated herein by reference.

Preferably, monoclonal antibodies that recognize an NKG2D epitope will react with an epitope that is present on a substantial percentage of $CD4^+$ T cells, particularly $CD4^+$ $CD28^-$ T cells, in patients such as rheumatoid arthritis patients, but will not significantly react with other cells, i.e., immune or non-immune cells that do not express NKG2D. Accordingly, once an antibody that specifically recognizes NKG2D on NK or T cells, preferably human NK or T cells, most preferably human $CD4^+$ T cells is identified, it can be tested for its ability to bind to T cells taken from patients with autoimmune or inflammatory disorders such as rheumatoid arthritis. It will be appreciated that the present invention can be used for the treatment of any disorder in which NKG2D activity is linked to the pathology of the disorder, regardless of the cell type expressing the receptor (e.g., $CD4^+$ T cells, $CD8^+$ T cells, NK cells, etc.), and the antibodies can be tested for their ability to bind to the receptor on whichever cell type is relevant for the particular disorder. For example, if it is observed that a particular disorder is associated with excess activity or proliferation of NKG2D-expressing NK cells, then the antibodies can be developed and tested using NK cells expressing the same receptor.

In one embodiment, the antibodies are validated in an immunoassay to test its ability to bind to NKG2D-expressing cells, e.g. $CD4^+CD28^-$ T cells taken from patients with rheumatoid arthritis. For example, peripheral blood lymphocytes (PBLs) are taken from a plurality of patients, and $CD4^+$, preferably $CD4^+CD28^-$, cells are enriched from the PBLs, e.g., by flow cytometry using relevant antibodies. The ability of a given antibody to bind to the cells is then assessed using standard methods well known to those in the art. Antibodies that are found to bind to a substantial proportion (e.g., 20%, 30%, 40%, 50%, 60%, 70%, 80% or more) of cells known to express NKG2D, e.g. NK cells, CD8 T cells, CD4 T cells from RA patients, etc., from a significant percentage of patients (e.g., 5%, 10%, 20%, 30%, 40%, 50% or more) are suitable for use in the present invention, both for diagnostic purposes to determine the expression of the NKG2D receptor in a patient's cells or for use in the herein-described therapeutic methods, e.g., for use as human-suitable blocking or, alternatively, cytotoxic antibodies. To assess the binding of the antibodies to the cells, the antibodies can either be directly or indirectly labeled. When indirectly labeled, a secondary, labeled antibody is typically added. The binding of the antibodies to the cells can then be detected using, e.g., cytofluorometric analysis (e.g. FACScan). Such method are well known to those of skill in the art.

Identifying Antibodies or Other Compounds that Interfere with NKG2D Activation

Antibodies found to specifically bind to NKG2D receptors, preferably human NKG2D receptors, as well as other molecules, can be assessed for their ability to inhibit the stimulation of the receptor by ligands. Any of a large number of assays, both molecular, cell-based, and animal-based models can be used. In typical embodiments, cell-based assays will be used in which cells expressing NKG2D are exposed to an NKG2D ligand (or cells expressing the ligand), and the ability of the antibody or a test compound to disrupt the stimulation of the receptor is assessed.

In one preferred embodiment, a cellular assay is used in which NKG2D-expressing cells, e.g., $CD4^+CD28^-$ cells from rheumatoid arthritis patients (or the equivalent cells from another autoimmune or inflammatory disorder) are incubated with an NKG2D ligand such as MICA, MICB, or a ULBP protein, or a cell expressing any of these ligands, and the ability of an anti-NKG2D antibody or other molecule to block the activation of the cell is assessed. In an alternative assay, a baseline level of activity for the NKG2D receptor is obtained in the absence of a ligand, and the ability of the antibody or compound to cause a decrease in the baseline activity level is detected. In one type of embodiment, a high-throughput screening approach is used to identify compounds capable of blocking the activation of the receptor or otherwise downregulating it.

Any of a number of cell-based assays can be used to assess NKG2D activity, including gene expression-based activities, cytotoxicity-based assays, and proliferation assays. Preferably, in vitro assays will use cells taken from patients with autoimmune or inflammatory disorders such as RA, e.g. $CD4^+CD28^-$ cells expressing NKG2D taken from (or cell lines derived therefrom) patients with RA, but in general any NKG2D-expressing cells can be used. For example, non-RA immune cell lines, e.g. T cell lines, can be transfected with an NKG2D-encoding transgene and used in the present assays, so long that the expression of the receptor alters the activity of the cells in a detectable way, e.g., renders them activatible by NKG2D ligand. It will be appreciated that, for such assays, any isoform of NKG2D can be used in such assays, e.g., the isoforms discussed in Diefenbach et al. (2002) Nat Immunol. 3(12):1142-9, the entire disclosure of which is herein incorporated by reference).

In one embodiment, cell lines will be established using $CD4^+CD28^-NKG2D^+$ cells from RA patients, e.g. PBLs or T cells isolated from synovial tissue. Such cells can be cultured in the presence of IL-15 to ensure continued expression of NKG2D (see, e.g., Groh et al. (2003) PNAS 100:9452-9457, the entire disclosure of which is herein incorporated by reference). In numerous embodiments, assays will be used using non-human cells or non-human NKG2D, e.g. mouse cells expressing either mouse or human NKG2D, with the inclusion of the appropriate ligand (e.g., in the case of mouse, Rae-1 and H-60).

Any suitable physiological change that reflects NKG2D activity can be used to assess the utility of a test compound or antibody. For example, one can measure a variety of effects, such as changes in gene expression, cell growth, cell proliferation, pH, intracellular second messengers, e.g., $Ca^{2+}$, IP3, cGMP, or cAMP, or activity such as cytotoxic activity or ability to activate other T cells. In one embodiment, the activity of the receptor is assessed by detecting the expression of NKG2D-responsive genes, e.g., CD25, IFN-gamma, or TNF-alpha (see, e.g., Groh et al. (2003) PNAS 100:9452-9457; André et al. (2004) Eur. J. Immunol 34:1-11). In one embodiment, NKG2D activity is assessed by incubating $CD4^+CD28^-NKG2D^+$ cells in the presence of a ligand or activating anti-NKG2D antibody, as well as an anti-CD3 antibody, and assessing the ability of the compound or test antibody to inhibit the release of TNF-alpha or IFN-gamma by the T cells. In another embodiment, $CD4^+CD28^-NKG2D^+$ T cells are incubated in the presence of ligand, e.g., MICA, MICB, ULBP-1, ULBP-2, ULBP-3, etc., or ligand-producing cells, e.g., autologous MIC+RA synoviocytes, and the ability of the test antibody or compound to inhibit cytokine production (e.g., IFN-gamma or TNF-alpha), or T cell proliferation, is assessed.

In animal-based assays, any physiological or pathological consequence of NKG2D activation in cells within the animal can be used to assess antibody or test compound activity. For example, in one embodiment, $CD4^+CD28^-NKG2D^+$ cells are introduced into the joints of an animal model, with or without co-administration of ligand producing cells such as MICA-producing synoviocytes, and inflammation or tissue damage is assessed. Test compounds or antibodies can then be introduced, and their ability to inhibit, slow, reverse, or in any way affect the inflammation or tissue damage is detected.

In addition to anti-NKG2D antibodies, other molecules can be tested in the present assays and, if activity is detected, used in methods to inhibit NKG2D stimulation in cells in vivo. The compounds can be any small chemical compound, or a biological entity, such as a protein, sugar, nucleic acid or lipid. Typically, test compounds will be small chemical molecules and peptides. Essentially any chemical compound can be used as a potential NKG2D blocking compound, although most often compounds that can be dissolved in aqueous or organic (especially DMSO-based) solutions are used. In general, assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In any of the herein-described assays, a decrease of 5%, 10%, 20%, preferably 30%, 40%, 50%, most preferably 60%, 70%, 80%, 90%, 95%, or greater reduction in any detectable measure of NKG2D-stimulated activity in the cells indicates that the test antibody or compound is a suitable candidate for use in the present methods. In other embodiments, the expression of NKG2D itself can be used to assess receptor activity, as normally ligands such as MIC ligands downregulate the receptor. Accordingly, compounds or antibodies that block ligand-induced NKG2D downregulation can also be identified as good candidates for the present methods (at the same time, other compounds that cause downregulation of the receptor through a mechanism other than receptor stimulation—e.g., by decreasing transcription or translation of the gene, are also desirable).

In one preferred embodiment, high throughput screening methods are used to identify small molecules or other compounds that are capable of blocking NKG2D activation in T or other cells. Such methods involve providing a combinatorial chemical or peptide library containing a large number of potential therapeutic compounds (potential modulator or binding compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghten et al., Nature 354:84-88 (1991)). Other chemistries for generating chemical diversity libraries can also be used. Such chemistries include, but are not limited to:peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligo-carbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g. U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos,

Rendering Anti-NKG2D Antibodies Suitable for Use in Humans

Monoclonal antibodies that can specifically bind and/or block the activation of NKG2D, e.g., in CD4+CD28− NKG2D+ T cells of rheumatoid arthritis patients, the antibodies will generally be modified so as to make them suitable for therapeutic use in humans. For example, they may be humanized, chimerized, or selected from a library of human antibodies using methods well known in the art. Such human-suitable antibodies can be used directly in the present therapeutic methods, or can be further derivatized into cytotoxic antibodies, as described infra, for use in the methods.

In one, preferred, embodiment, the DNA of a hybridoma producing an antibody of this invention, e.g. an ON72-like antibody, can be modified prior to insertion into an expression vector, for example, by substituting the coding sequence for human heavy- and light-chain constant domains in place of the homologous non-human sequences (e.g., Morrison et al. (1984) *PNAS* 81:6851), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

In one particularly preferred embodiment, the antibody of this invention is humanized. "Humanized" forms of antibodies according to this invention are specific chimeric immunoglobulins, immunoglobulin chains or fragments thereof (such as Fv, Fab, Fab', F(ab')$_2$, or other antigen-binding subsequences of antibodies) which contain minimal sequence derived from the murine or other non-human immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody. In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. For further details see Jones et al. (1986) Nature 321: 522; Reichmann et al. (1988) Nature 332:323; Verhoeyen et al. (1988) Science 239:1534 (1988); Presta (1992) Curr. Op. Struct. Biol. 2:593; each of which is herein incorporated by reference in its entirety.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence which is closest to that of the mouse is then accepted as the human framework (FR) for the humanized antibody (Sims et al. (1993) J. Immun., 151:2296; Chothia and Lesk (1987) J. Mol. Biol. 196:901). Another method uses a particular framework from the consensus sequence of all human antibodies of a particular subgroup of light or heavy chains. The same framework can be used for several different humanized antibodies (Carter et al. (1992) PNAS 89:4285; Presta et al. (1993) J. Immunol. 51:1993)).

It is further important that antibodies be humanized while retaining their high affinity for NKG2D, preferably human NKG2D, and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Human antibodies may also be produced according to various other techniques, such as by using, for immunization, other transgenic animals that have been engineered to express a human antibody repertoire. In this technique, elements of the human heavy and light chain loci are introduced into mice or other animals with targeted disruptions of the endogenous heavy chain and light chain loci (see, e.g., Jakobovitz et al. (1993) Nature 362:255; Green et al. (1994) Nature Genet. 7:13; Lonberg et al. (1994) Nature 368:856; Taylor et al. (1994) Int. Immun. 6:579, the entire disclosures of which are herein incorporated by reference). Alternatively, human antibodies can be constructed by genetic or chromosomal transfection methods, or through the selection of antibody repertoires using phage display methods. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell (see, e.g., Johnson et al. (1993) Curr Op Struct Biol 3:5564-571; McCafferty et al. (1990) Nature 348:552-553, the entire disclosures of which are herein incorporated by reference). Human antibodies may also be generated by in vitro activated B cells (see, e.g., U.S. Pat. Nos. 5,567,610 and 5,229,275, the disclosures of which are incorporated in their entirety by reference).

In one embodiment, "humanized" monoclonal antibodies are made using an animal such as a XenoMouse® (Abgenix, Fremont, Calif.) for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference. An analogous method can be achieved using a HuMAb-Mouse™ (Medarex).

The antibodies of the present invention may also be derivatized to "chimeric" antibodies (immunoglobulins) in which a portion of the heavy and/or light chain is identical with or homologous to corresponding sequences in the original antibody, while the remainder of the chain(s) is identical with or homologous to corresponding sequences in antibodies derived from another species or belonging to another antibody class or subclass, as well as fragments of such antibodies, so long as they exhibit the desired biological activity (see, e.g., Morrison et al. (1984) PNAS 81:6851; U.S. Pat. No. 4,816,567).

Making Human-suitable Antibodies Cytotoxic

While most blocking NKG2D antibodies will be used without derivitization, simply based on their ability to block stimulation of the NKG2D receptor by ligands, in certain embodiments the antibodies (or other compounds) will be derivatized to make them toxic to cells. In this way, administration of the antibody to rheumatoid arthritis patients, e.g., directly in affected joints, will lead to the relatively specific binding of the antibody to NKG2D-expressing cells, e.g., $CD4^+CD28^-NKG2D^+$ cells, thereby directly killing or inhibiting these cells which contribute to the pathology of the disorder. Because of the specificity of the treatment, other, non-NKG2D-expressing cells of the body, including most other $CD4^+$ T cells, as well as other cells of the immune system and other non-immune cells, will be minimally affected by the treatment. In one embodiment, cytotoxic anti-NKG2D antibodies are used in conjunction with cytotoxic anti-CD4 antibodies, e.g., each of them being administered at moderate levels (or using moderately-cytotoxic agents), so that only cells expressing both antigens will be bound by both antibodies and efficiently killed.

Any of a large number of toxic moieties or strategies can be used to produce such antibodies. In certain, preferred embodiments, the antibodies will be directly derivatized with radioisotopes or other toxic compounds. In such cases, the labeled monospecific antibody can be injected into the patient, where it can then bind to and kill cells expressing the target antigen, with unbound antibody simply clearing the body. Indirect strategies can also be used, such as the "Affinity Enhancement System" (AES) (see, e.g., U.S. Pat. No. 5,256, 395; Barbet et al. (1999) Cancer Biother Radiopharm 14:153-166; the entire disclosures of which are herein incorporated by reference). This particular approach involves the use of a radiolabeled hapten and an antibody that recognizes both the NKG2D and the radioactive hapten. In this case, the antibody is first injected into the patient and allowed to bind to target cells, and then, once unbound antibody is allowed to clear from the blood stream, the radiolabeled hapten is administered. The hapten binds to the antibody-antigen complex on the overproliferating LGL (e.g. NK) cells, thereby killing them, with the unbound hapten clearing the body.

Any type of moiety with a cytotoxic or cytoinhibitory effect can be used in conjunction with the present antibodies to inhibit or kill specific NK receptor expressing cells, including radioisotopes, toxic proteins, toxic small molecules, such as drugs, toxins, immunomodulators, hormones, hormone antagonists, enzymes, oligonucleotides, enzyme inhibitors, therapeutic radionuclides, angiogenesis inhibitors, chemotherapeutic drugs, vinca alkaloids, anthracyclines, epidophyllotoxins, taxanes, antimetabolites, alkylating agents, antibiotics, COX-2 inhibitors, SN-38, antimitotics, antiangiogenic and apoptotoic agents, particularly doxorubicin, methotrexate, taxol, CPT-11, camptothecans, nitrogen mustards, gemcitabine, alkyl sulfonates, nitrosoureas, triazenes, folic acid analogs, pyrimidine analogs, purine analogs, platinum coordination complexes, *Pseudomonas* exotoxin, ricin, abrin, 5-fluorouridine, ribonuclease (RNase), DNase I, Staphylococcal enterotoxin-A, pokeweed antiviral protein, gelonin, diphtherin toxin, *Pseudomonas* exotoxin, and *Pseudomonas* endotoxin and others (see, e.g., Remington's Pharmaceutical Sciences, 19th Ed. (Mack Publishing Co. 1995); Goodman and Gilman's The Pharmacological Basis of Therapeutics (McGraw Hill, 2001); Pastan et al. (1986) Cell 47:641; Goldenberg (1994) Cancer Journal for Clinicians 44:43; U.S. Pat. No. 6,077,499; the entire disclosures of which are herein incorporated by reference). It will be appreciated that a toxin can be of animal, plant, fungal, or microbial origin, or can be created de novo by chemical synthesis.

The toxins or other compounds can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (see, e.g., Yu et al. (1994) Int. J. Cancer 56:244; Wong, Chemistry of Protein Conjugation and Cross-linking (CRC Press 1991); Upeslacis et al., "Modification of Antibodies by Chemical Methods," in Monoclonal antibodies:principles and applications, Birch et al. (eds.), pages 187-230 (Wiley-Liss, Inc. 1995); Price, "Production and Characterization of Synthetic Peptide-Derived Antibodies," in Monoclonal antibodies:Production, engineering and clinical application, Ritter et al. (eds.), pages 60-84 (Cambridge University Press 1995), Cattel et al. (1989) Chemistry today 7:51-58, Delprino et al. (1993) J. Pharm. Sci 82:699-704; Arpicco et al. (1997) Bioconjugate Chernistry 8:3; Reisfeld et al. (1989) Antihody, Immunicon. Radiopharm. 2:217; the entire disclosures of each of which are herein incorporated by reference).

In one, preferred, embodiment, the antibody will be derivatized with a radioactive isotope, such as I-131. Any of a number of suitable radioactive isotopes can be used, including, but not limited to, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-105, Palladium-109, Praseodymium-143, Promethium-149, Erbium-169, Iridium-194, Gold-198, Gold-199, and Lead-211. In general, the radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Also preferred are radionuclides that substantially decay with generation of alpha-particles.

In selecting a cytotoxic moiety for inclusion in the present methods, it is desirable to ensure that the moiety will not exert significant in vivo side effects against life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The term "significant side effects", as used herein, refers to an antibody, ligand or antibody conjugate, that, when administered in vivo, will produce only negligible or clinically manageable side effects, such as those normally encountered during chemotherapy.

Validating Antibodies and other Compounds

Once antibodies are obtained that are known to specifically bind to NKG2D on cells from patients with rheumatoid arthritis or related disorders, and which have been rendered suitable for use in humans, and optionally derivatized to include a toxic moiety, they will generally be assessed for their ability to interact with, affect the activity of, and/or kill target cells. In general, the assays described above for detecting antibody binding to NKG2D-expressing cells, including competition-based assays, ELISAs, radioimmunoassays, Western blotting, BIACORE-based assays, and flow cytometry assays, can be equally applied to detect the interaction of humanized, chimeric, or other human-suitable, anti-NKG2D antibodies with NKG2D-expressing target cells. Typically, target cells will be T cells, preferably $CD4^+CD28^-$ T cells taken from patients with rheumatoid arthritis or another autoimmune or inflammatory disorder.

In such assays, the ability of the humanized or human-suitable, optionally cytotoxic antibody to bind to the target cell or human NKG2D will be compared with the ability of a control protein, e.g. an antibody raised against a structurally unrelated antigen, or a non-Ig peptide or protein, to bind to the same target. Antibodies or fragments that bind to the target cells or NKG2D using any suitable assay with 25%, 50%, 100%, 200%, 1000%, or higher increased affinity relative to the control protein, are said to "specifically bind to" or "specifically interact with" the target, and are preferred for use in the therapeutic methods described below.

In addition to binding, the ability of antibodies to inhibit the proliferation or activation of, or, in the case of cytotoxic antibodies, kill, target cells can be assessed. In one embodiment, human T cells expressing the NKG2D receptor, e.g., $CD4^+CD28^-$ T cells taken from rheumatoid arthritis patients, are introduced into plates, e.g., 96-well plates, and exposed to various amounts of the relevant antibodies. For cytotoxic antibodies, by adding a vital dye, i.e. one taken up by intact cells, such as AlamarBlue (BioSource International, Camarillo, Calif.), and washing to remove excess dye, the number of viable cells can be measured by virtue of the optical density (the more cells killed by the antibody, the lower the optical density). (See, e.g., Connolly et al. (2001) J Pharm Exp Ther 298:25-33, the disclosure of which is herein incorporated by reference in its entirety). Any other suitable in vitro cytotoxicity assay, assay to measure cell proliferation or survival, or assay to detect T cell activity can equally be used, as can in vivo assays, e.g. administering (e.g., to the joints) the antibodies to animal models, e.g., mice, containing human T cells, e.g., $CD4^+CD28^-$ T cells expressing NKG2D, and preferably ligand (such as MICA or MICB) expressing cells, and detecting the effect of the antibody administration on the survival or activity of the human T cells over time, or on joint erosion in the case of RA models. Also, where the antibody cross-reacts with a non-human receptor, e.g., a primate NKG2D, the therapeutic antibodies can be used in vitro or in vivo to assess the ability of the antibody to bind to, affect the activity of, and/or kill T or other cells from the animal that express the receptor.

Any antibody, preferably a human-suitable antibody, e.g. a cytotoxic antibody, that can detectably slow, stop, or reverse the proliferation or activity of NKG2D-expressing T cells, in vitro or in vivo, can be used in the present methods. Preferably, the antibody is capable of blocking or reversing the activation of the cells, leading to a decrease in the total activity of the T cells, e.g., CD4+ T cells, and thus alleviating the pathology of the disorder. In certain embodiments, the antibody is capable of producing a 10%, 20%, 30%, 40%, 50%, 60%, 70%, 80%, 90%, 95%, 96%, 97%, 98%, 99%, or 100% decrease in the number of T cells expressing the receptor, or in the activity of all or a subset of cells expressing the receptor.

It will be appreciated that equivalent methods can be used to produce antibodies or other compounds suitable for treating animals, or for testing in an animal model. In that case, the antibodies will be ensured to be capable of specifically recognizing NKG2D from the relevant animal. Similarly, the antibody will be modified to be suitable for administration into the particular animal.

Administration of Antibodies and Other Compounds for Treatment Methods

The antibodies produced using the present methods are particularly effective at treating autoimmune and inflammatory disorders, most particularly rheumatoid arthritis. In general, the present methods can be used to treat any disorder caused at least in part by the presence or activity of NKG2D-expressing cells, e.g., T cells such as $CD4^+CD28^-$ cells expressing NKG2D, and which can therefore be effectively treated by selectively killing or inhibiting the activation of NKG2D-expressing cells, e.g., by inhibiting the activation of or by downregulating the expression of the receptor. Other suitable diseases include other autoimmune disorders and inflammatory disorders, particularly those involving $CD4^+$ cells, particularly $CD4^+CD28^-$, cells such as Wegener's granulomatosis, Sjogren's syndrome, and insulin-dependent diabetes mellitus. In any case, however, any disorder whose pathology involves at least in part NKG2D-mediated cell activation, can be treated. In one embodiment, the methods can be used to treat a disease other than insulin-dependent diabetes mellitus. In another embodiment, the methods are used to treat a disorder other than an inflammatory disorder of the intestinal epithelium.

In some embodiments, prior to the administration of the NKG2D blocking compound or antibody, the expression of NKG2D on cells underlying the particular disorder will be assessed. This can be accomplished by obtaining a sample of PBLs or cells from the site of the disorder (e.g., from the synovium in RA patients), and testing e.g., using immunoassays, to determine the relative prominence of markers such as CD4, CD8, CD28, etc., as well as NKG2D on the cells. Other methods can also be used to detect expression of NKG2D and other genes, such as RNA-based methods, e.g., RT-PCR or Northern blotting.

The treatment may involve multiple rounds of antibody or compound administration. For example, following an initial round of administration, the level and/or activity of NKG2D-expressing T cells, e.g., $CD4^+CD28^-$ T cells in the patient will generally be re-measured, and, if still elevated, an additional round of administration can be performed. In this way, multiple rounds of receptor detection and antibody or compound administration can be performed, e.g., until the disorder is brought under control.

The invention also provides compositions, e.g., pharmaceutical compositions, that comprise any of the present antibodies or other compounds, including fragments and derivatives thereof, in any suitable vehicle in an amount effective to inhibit the activation of NKG2D, or the proliferation or activity of, or to kill, NKG2D-expressing cells in patients. The compositions generally further comprise a pharmaceutically acceptable carrier. It will be appreciated that the present methods of administering antibodies and compositions to patients can also be used to treat animals, or to test the efficacy of any of the herein-described methods or compositions in animal models for human diseases.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. For localized disorders such as RA, the compositions will often be administered topically, e.g., in inflamed joints.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. Such compositions are prepared according to techniques well-known in the art of pharmaceutical formulation.

The compositions of this invention may be administered topically, especially when the target of treatment includes areas or organs readily accessible by topical application, including diseases of the eye, the skin, the joints, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions may be formulated in an ointment such as petrolatum.

The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In one embodiment, the antibodies or therapeutic compounds of this invention may be incorporated into liposomes ("immunoliposomes" in the case of antibodies), alone or together with another substance for targeted delivery to a patient or an animal. Such other substances can include nucleic acids for the delivery of genes for gene therapy or for the delivery of antisense RNA, RNAi or siRNA for suppressing a gene in a T cell, or toxins or drugs for the activation of T cells through other means, or any other agent described herein that may be useful for activation of T cells.

In another embodiment, the antibodies or other compounds of the invention can be modified to improve its bioavailability, half life in vivo, etc. For example, antibodies and other compounds can be pegylated, using any of the number of forms of polyethylene glycol and methods of attachment known in the art (see, e.g., Lee et al. (2003) Bioconjug Chem. 14(3):546-53; Harris et al. (2003) Nat Rev Drug Discov. 2(3):214-21; Deckert et al. (2000) Int J Cancer. 87(3):382-90).

Several monoclonal antibodies have been shown to be efficient in clinical situations, such as Rituxan (Rituximab), Herceptin (Trastuzumab) Xolair (Omalizumab), Bexxar (Tositumomab), Campath (Alemtuzumab), Zevalin, Oncolym and similar administration regimens (i.e., formulations and/or doses and/or administration protocols) may be used with the antibodies of this invention. Schedules and dosages for administration can be determined in accordance with known methods for these products, for example using the manufacturers' instructions. For example, a monoclonal antibody can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody of the invention may between about 10 mg/m2 and 500 mg/m2. However, it will be appreciated that these schedules are exemplary and that optimal schedule and regimen can be adapted taking into account the affinity and anti-NKG2D activity of the antibody and the tolerability of the antibodies that must be determined in clinical trials. Quantities and schedule of injection of antibodies to NKG2Ds that saturate cells for 24 hours, 48 hours 72 hours or a week or a month will be determined considering the affinity of the antibody and the its pharmacokinetic parameters.

For non-antibody compounds, the dose administered to a patient should be sufficient to effect a beneficial response in the subject over time. The dose will be determined by the efficacy of the particular modulators employed and the condition of the subject, as well as the body weight or surface area of the area to be treated. The size of the dose also will be determined by the existence, nature, and extent of any adverse side-effects that accompany the administration of a particular compound or vector in a particular subject. In determining the effective amount of the compound to be administered, a physician may evaluate circulating plasma levels of the compound, compound toxicities, and the production of anti-compound antibodies. In general, the dose equivalent of a compound is from about 1 ng/kg to 10 mg/kg for a typical subject. Administration can be accomplished via single or divided doses.

According to another important embodiment of the present invention, the anti-NKG2D antibodies and/or other compounds may be administered in conjunction with one or more additional therapeutic agents, including agents normally utilized for the particular therapeutic purpose for which the antibody or compound is being administered, e.g. for treatment of RA. The other agents can either be administered together with the present antibody or compound, i.e., in the same pharmaceutical composition, or may be administered separately, including temporally. The additional therapeutic agent will generally be administered at a dose typically used for that agent in a monotherapy for the particular disease or condition being treated. Such therapeutic agents include, but are not limited to, therapeutic agents used in the treatment of autoimmune disorders, therapeutic agents used in the treatment of inflammatory disorders, therapeutic agents used in the treatment of rheumatoid arthritis, therapeutic agents used in the treatment of Wegener's granulomatosis, therapeutic agents used in the treatment of Sjogren's syndrome, therapeutic agents used in the treatment of insulin-dependent diabetes mellitus, cytokines such as IL-10, inhibitors of NKG2D ligands such as anti-MICA antibodies and other compounds, anti-MICB antibodies and other compounds, anti-ULBP-1 antibodies and other compounds, anti-ULBP-2 antibodies and other compounds, anti-ULBP-3 antibodies and other compounds, and compounds that counteract cytokines and other molecules that drive NKG2D expression, e.g., anti-TNF-alpha antibodies and other compounds, and anti-IL-15 antibodies and other compounds. So long as a particular therapeutic approach is not known to be detrimental to the patient's condition in itself, and does not significantly counteract the NKG2D antibody- or compound-based treatment, its combination with the present invention is contemplated.

The present invention is based in part on the discovery that the pathology of RA and other disorders is related to the presence of, and proliferation of, NKG2D ligand (e.g., MICA and MICB) expressing cells in areas of the body outside of the intestinal epithelium, and the coincidental presence of NKG2D-expressing T cells, particularly $CD4^+$ T cells such as $CD4^+CD28^-$ T cells. The binding of the NKG2D ligands to NKG2D on T cells in these areas, e.g., in the joints of RA patients, leads to inflammation and T cell activation that contributes to the pathology of disorders such as RA. Accordingly, in junction with the administration of compounds or antibodies that block NKG2D activation, it is specifically envisioned to administer other compounds or antibodies that can inhibit other aspects of these local pathological interactions. For example, antibodies or other compounds that bind to or otherwise inhibit NKG2D ligands, such as MICA or MICB, can be administered, as can antibodies or other inhibitors of cytokines that drive NKG2D expression, such as IL-15 and TNF-alpha. Also, IL-10 can be used as well, as it can downregulate NKG2D.

The present invention may be used in combination with classical approaches, such as surgery, and the like. When one or more agents or approaches are used in combination with the present therapy, there is no requirement for the combined results to be additive of the effects observed when each treatment is conducted separately. Although at least additive effects are generally desirable, any decrease in NKG2D activity or other beneficial effect above one of the single therapies would be of benefit. Also, there is no particular requirement for the combined treatment to exhibit synergistic effects, although this is certainly possible and advantageous. The NKG2D-based treatment may precede, or follow, the other treatment by, e.g., intervals ranging from minutes to weeks and months. It also is envisioned that more than one administration of either the anti-NKG2D composition or the other agent will be utilized. The agents may be administered interchangeably, on alternate days or weeks; or a cycle of anti-NKG2D treatment may be given, followed by a cycle of the other agent therapy. In any event, all that is required is to deliver both agents in a combined amount effective to exert a therapeutically beneficial effect, irrespective of the times for administration.

In other aspects, immunomodulatory compounds or regimens may be practiced in combination with the present invention. Preferred examples include treatment with cytokines. Various cytokines may be employed in such combined approaches. Examples of cytokines include IL-1alpha IL-1beta, IL-2, IL-3, IL-4, IL-5, IL-6, IL-7, IL-8, IL-9, IL-10, IL-11, IL-12, IL-13, IL-15, IL-21, TGF-beta, GM-CSF, M-CSF, G-CSF, TNF-alpha, TNF-beta, LAF, TCGF, BCGF, TRF, BAF, BDG, MP, LIF, OSM, TMF, PDGF, IFN-alpha, IFN-beta, IFN-gamma, or compounds that inhibit any of these cytokines. Cytokines or their inhibitors are administered according to standard regimens, consistent with clinical indications such as the condition of the patient and the relative toxicity of the cytokine.

The present methods can also be used in combination with adjunct compounds. Adjunct compounds may include by way of example anti-emetics such as serotonin antagonists and therapies such as phenothiazines, substituted benzamides, antihistamines, butyrophenones, corticosteroids, benzodiazepines and cannabinoids; bisphosphonates such as zoledronic acid and pamidronic acid; and hematopoietic growth factors such as crythropoietin and G-CSF, for example filgrastim, lenograstim and darbepoietin.

The present antibodies and/or compounds can be included in kits, which may contain any number of antibodies and/or other compounds, e.g., 1, 2, 3, 4, 5, 6, 7, 8, 9, 10, or any other number of therapeutic antibodies and/or compounds, as well as, in certain embodiments, antibodies or other diagnostic reagents for detecting the expression of NKG2D and other molecules on cells. Such diagnostic antibodies will often be labeled, either directly or indirectly (e.g., using secondary antibodies). Therapeutic antibodies can be either modified, e.g. by the addition of a cytotoxic agent, or unmodified, working, e.g., by blocking NKG2D activation, or by simply binding to target cells and thereby inactivating them, triggering cell death, or marking them for destruction by the immune system. It will be appreciated that this description of the contents of the kits is not limiting in any way. For example, the kit may contain other types of therapeutic compounds as well, such as other anti-inflammatory agents, agents against NKG2D ligands such as MICA, MICB, or ULBP, or agents against molecules that drive NKG2D expression, e.g., anti-TNF-alpha or anti-IL-15 agents, or IL-10. Preferably, the kits also include instructions for using the antibodies or other compounds, e.g., detailing the herein-described methods.

Further aspects and advantages of this invention are disclosed in the following experimental section, which should be regarded as illustrative and not limiting the scope of this application.

EXAMPLES

Example 1

Materials and Methods

Peripheral Blood Samples Tissue Materials, and Cell Preparations. Peripheral blood was obtained from 30 unrelated patients fulfilling the 1988 American College of Rheumatology criteria for RA and from 20 random healthy volunteers. Synovial tissues were obtained from 19 RA and 2 osteoarthritis patients at the time of joint arthroplasty or by closed-needle synovial biopsy. Five peripheral blood and synovial tissue samples were matched; the remainder were from different patient populations. These activities were approved by local institutional review boards, and all subjects gave written informed consent. Peripheral blood mononuclear cells (PBMC) were isolated by Ficoll-Hypaque density gradient centrifugation. CD4 T cells were purified from unseparated peripheral blood by negative selection using a RosetteSep (StemCell Technologies, Vancouver) enrichment mixture. NKG2D− CD4 T cells were isolated from purified CD4 T cell populations with a FACSVantage cell sorter (BD Biosciences, San Diego) after immunofluorescence staining with anti-NKG2D mAb 1D11 [PDB] and phycoerythrin-goat anti-mouse Ig F(ab')2. For isolation of synovial cells, tissues were minced, partially digested with 0.3 mg/ml collagenase (Sigma), pressed through a metal screen, and centrifuged through Ficoll-Hypaque.

Flow Cytometry and Immunohistochemistry. PBMC, synovial mononuclear cells, and unseparated synoviocyte suspensions were examined by two- or three-color flow cytometry using various combinations of anti-CD3, -CD4, -CD8, -CD56, -TCR, -CD28, -CD45RA, or -CD45RO (BD PharMingen) conjugated to phycoerythrin, FITC, or PerCP. Binding of anti-NKG2D and anti-Ki-67 (BD PharMingen) mAbs was detected with phycoerytlirin- or FITC-goat anti-mouse Ig F(ab')2. Biotinylated anti-MIC mAb 6D4 was detected with streptavidin-FITC. For intracellular staining, cells were permeabilized with 0.1% saponin for 10 min at 4° C. before antibody exposure. For immunohistochemistry staining, 4-μm cryostat sections were made from synovial tissues embedded in OCT compound (Sakura Fine Technologies, Tokyo) and snap-frozen in liquid nitrogen. Sections were fixed in acetone, air dried, rehydrated in TBS, and blocked sequentially with 0.03% hydrogen peroxide, 25% normal goat serum, and 25% pooled human serum, all in TBS. Sections were incubated with anti-MIC mAb 6D4, anti-NKG2D mAb 1D11 [PDB], or isotype-matched IgG for 1 h at room temperature in a humid chamber. Antibody binding was detected by using biotinylated secondary IgG and streptavidin-horseradish peroxidase (DAKO). Sections were counterstained with Harris' hematoxylin and mounted with Glycergel (DAKO).

Induction of NKG2D and Generation of T Cell Clones and Synovial Fibroblast Cell Lines. PBMC from healthy volunteers and purified CD4+NKG2D− T cells from RA patients were cultured in RPMI medium 1640, 10% FCS, and antibiotics with or without IL-15 (15 ng/ml), tumor necrosis factor (TNF-) (15 ng/ml), IL-10 (20 ng/ml), IL-12 (20 ng/ml), or IFN- (10 ng/ml) (R & D Systems) for up to 10 days. T cells were tested for NKG2D expression before and at various time points after cytokine exposure by flow cytometry. In some experiments, CD4 T cells were stimulated with solid-phase anti-CD3 (OKT3, 50 ng/ml; Orthobiotech, Raritan, N.J.). For generation of T cell clones, CD4+CD28−NKG2D+ T cells were sorted from RA PBMC and synovial cell suspensions and seeded at 0.5 cells per well in 96-well round-bottom microtiter plates by using a FACSVantage cell sorter. T cells were cultured with weekly restimulations with -irradiated allogeneic PBMC (105 cells per well) in RPMI medium 1640 supplemented with 8% FCS, 2% pooled human serum, antibiotics, and IL-2 (5 units/ml; Chiron). RA synovial fibroblast cultures were established from cell suspensions prepared from two biopsies (see above) by adherence to tissue culture plates followed by removal of nonadherent cells. Adherent cells were cultured in DMEM supplemented with 10% FCS, 1 mM nonessential amino acids, 1 mM sodium pyruvate, and antibiotics. After four passages, cultures were free of contaminating mononuclear cells and expressed high levels of MIC as confirmed by flow cytometry.

RNA Blot Hybridization. Total cellular RNA was extracted and purified from freshly isolated CD4 T cells and CD4 T cells cultured in the presence of cytokines by using STAT-60 reagent (Tel-Test, Friendswood, Tex.). Standard procedures were followed for gel electrophoresis and blot hybridization.

Cytotoxicity, Cytokine Release, and T Cell Proliferation Assays. T cell cytolytic activity was tested in standard 4-h 51 Cr release assays with labeled target cells that included the mouse mastocytoma P815 cell line for redirected lysis and MICA transfectants of the B-lymphoblastoid C1R cell line. Redirected lysis was tested in the presence of anti-NKG2D and anti-CD3 (OKT3) mAbs or isotype controls, each at a concentration of 2 μg/ml. Assays were done in triplicate, and results were scored according to the standard formula. In the cytokine release assays, resting (14 days after stimulation) T cells (105 per well) were stimulated with either solid-phase anti-CD3 with or without anti-NKG2D or control Ig as described or with equal numbers of autologous or mismatched irradiated synovial fibroblasts. For blocking experiments, effector or stimulator cells were incubated with saturating amounts of anti-NKG2D, anti-MIC (mAb 6D4), or control IgG 30 min before and throughout the coculture. After 24 h, T cell supernatants were collected from triplicate wells and pooled. Secreted IFN- and TNF-were quantitated by commercial ELISA with matched antibody pairs in relation to standard pairs (R & D Systems). T cell proliferation was measured with resting T cells (105 cells per well) after activation with solid-phase mAb as described above. Cultures were pulsed with [3H]thymidine on day 3 and collected after 12 h by using a micromate cell harvester (Packard). Incorporated radioactivity was determined by using Uni-Filter GF/C plates (Packard) and a TopCount liquid scintillation counter (Packard).

ELISA of Soluble MICA and Modulation of NKG2D. Five serum samples matched with MIC-positive synovial biopsies and five unmatched serum samples from RA patients were tested for the presence of soluble MICA by ELISA as described. Modulation of NKG2D on peripheral blood CD4 T cells among PBMC from RA patients by soluble MIC containing RA sera (1:5 dilutions of sera) in the presence or absence of neutralizing mAb against IL-15 (0.5 µg/ml) and TNF-(0.2 µg/ml; R & D Systems) was examined after 24 h of incubation by staining with anti-CD4 and anti-NKG2D and flow cytometry. As a control experiment, T cells were exposed to the soluble MIC+ BT 450-85 serum from a breast cancer patient, which down-modulates NKG2D on CD8 T cells. The amounts of IL-15 and TNF- in patient sera were determined by commercial ELISA with matched antibody pairs in relation to standard pairs (R & D Systems).

Example 2

CD4$^+$CD28$^-$ T Cells from RA Patients Express NKG2D

Peripheral blood lymphocytes (PBL) from 30 RA patients and 20 healthy volunteers were profiled for NKG2D expression by antibody staining and flow cytometry. The amounts and distribution of NKG2D among RA CD8 T cells, NK cells, and T cells were similar to those recorded with the control. However, 11-61% (mean 18%) of RA CD4 T cells were positive for NKG2D, whereas nearly all control CD4 T cells were negative. We examined whether NKG2D expression was associated with CD4$^+$CD28$^-$ T cells by multicolor flow cytometry. Consistent with previous observations, these T cells occurred among all RA but not normal PBL, at frequencies ranging from 12% to 50% (mean 15%). With all RA PBL samples, NKG2D was preferentially expressed on CD4$^+$CD28$^-$ T cells, with positive cell numbers ranging from 35% to 100% (mean 47%). By contrast, NKG2D was present on 3-36% (mean 8%) of CD4$^+$CD28$^+$ T cells. In four cases, large expansions of CD4$^+$CD28$^-$ T cells (28-50%) correlated with disproportionately higher numbers of NKG2D$^+$ cells (80-100%), suggesting an involvement of NKG2D in T cell proliferation. Altogether, however, there was no significant relationship between the proportion of these T cells and the frequency of expression of NTKG2D.

RA CD4$^+$CD28$^-$ T cells also occur at sites of tissue injury, including synovial joints and rheumatoid vasculitis. As with circulating RA CD4 T cells, NKG2D was present on synovial tissue CD4 T cells, preferentially on those lacking CD28, whereas its expression on other lymphocyte infiltrates was unchanged. Thus, circulating and resident CD4 T cells from patients with RA frequently expressed NKG2D. Its main occurrence among the autoreactive CD28$^-$ subset suggests that it may participate in tissue destruction. NKG2D was also present on variable proportions of RA CD4$^+$CD28$^+$ T cells and was associated with a memory phenotype as indicated by CD45 isotype expression.

Example 3

Induction of NKG2D on CD4 T Cells by IL-15 and TNF-Alpha

Under normal conditions, the tissue distribution of the MIC ligands of NKG2D is limited to intestinal epithelium where intraepithelial CD8 T cells have diminished expression of NKG2D as a result of ligand-induced down-modulation. However, NKG2D can be up-regulated on these T cells by IL-15, which is prominent among the proinflammatory cytokines that are abundant in RA synovia. We tested whether IL-15 might be responsible for the aberrant expression of NKG2D on RA CD4 T cells. Normal PBL were cultured in the presence or absence of IL-15 for several days, and surface NKG2D on lymphocyte subsets was monitored by flow cytometry. With CD8 T cells and NK cells, IL-15 had no effect on NKG2D expressed at maximum levels. However, NKG2D was progressively induced on CD4 T cells, with small positive populations (5-10% of CD4 T cells) appearing as early as 48 h after addition of IL-15. Maximum induction was reached after 6-7 days of culture, with 30-40% of CD4 T cells expressing NKG2D. Thereafter, NKG2D decreased gradually unless the culture was replenished with fresh IL-15. A similar but markedly accelerated induction of NKG2D was observed with sorted RA CD4$^+$NKG2D$^-$ T cells. Already after 24 h, 10-20% of the T cells expressed NKG2D, and the majority was positive after 3 days. As indicated by intracellular staining of permeabilized cells, the more rapid appearance of surface NKG2D was likely due to redistribution of intracellular protein in a subpopulation of the RA CD4$^+$NKG2D$^-$ T cells, whereas the delayed response was due to induction of mRNA. As with IL-15, TNF-alpha is a key cytokine in the immunopathology of RA and induced NKG2D expression on CD4$^+$NKG2D$^-$ T cells among control and RA PBL; data not shown). The presence of both cytokines was confirmed in all of 10 RA peripheral blood serum samples, at concentrations of 6.4-13.3 pg/ml (mean 8.2 pg/ml) and 16.5-52.2 pg/ml (mean 24.4 pg/ml), respectively. Exposure to IL-10, but not to IL-12 and IFN-gamma, resulted in less pronounced and variable induction of NKG2D. T cell antigen receptor complex stimulation with anti-CD3 transiently induced NKG2D on some CD4 T cells.

Example 4

Aberrant Expression of MIC in RA Synovium

To explore the significance of CD4 T cell expression of NKG2D in the immunopathology of RA, frozen sections of disease synovial tissue specimens were tested for the presence of MIC by immunohistochemistry using mAb 6D4, which is specific for MICA and MICB, and isotype-matched negative control antibody. As observed by peroxidase substrate staining, all tissue specimens contained numerous positive cells. MIC$^+$ synoviocytes of spindle-shaped fibroblast-like and more rounded morphologies were distributed throughout the synovial lining and sublining areas and were often located close to, or interspersed with, lymphocytic aggregates. They were in close contact with NKG2D$^+$ lymphocytes, presumably CD4$^+$ T cells that were present throughout the synovial lining and in organized lymphoid microstructures. Rheumatoid synovial hyperplasia consists of fibroblasts and activated macrophages. The former have features of immortalized transformed cells and proliferate aggressively, which may explain the induced expression of MIC. This was confirmed by two-color staining of permeabilized synovial cell suspensions with antibodies against the nuclear Ki-67 proliferation marker and MIC. Analysis by flow cytometry revealed that the presence of MIC was strongly but not completely associated with expression of Ki-67. Control staining of cell suspensions derived from osteoarthritis tissue specimens gave negative results. Thus, in accord with previous evidence obtained with fibroblast and epithelial cell lines, expression of MIC was induced in proliferating rheumatoid synoviocytes.

Example 5

NKG2D Stimulates $CD4^+CD28^-$ T Cell Autoreactivity $CD4^+CD28^-$ T cells resemble NKT cells as they secrete large amounts of IFN-gamma and express perforin and granzyme B, which confer cytotoxic capacity. To test the function of NKG2D, we established each five $CD4^+CD28^-$ $NKG2D^+$ T cell clones from one RA synovial tissue specimen and two RA PBL samples. These clones represented a small minority of 2%, as most of the sorted T cells grown in culture lost NKG2D in the absence of IL-15. In antibody-dependent cytotoxicity assays, ligation of NKG2D did not induce redirected lysis of $FcgammaR^+$ mouse mastocytoma P815 cells by any of the 15 T cell clones, although anti-CD3 was effective, thus confirming their cytotoxic capacity. Consistent with previous results obtained with antigen-specific CD8 T cells, no cytotoxicity was scored against the CIR-MICA transfectant B-cell line. However, mAb crosslinking of NKG2D strongly augmented anti-CD3-triggered release of IFN-gamma and TNF-alpha by all T cell clones and stimulated T cell proliferation. Crosslinking of NKG2D alone had no effect. Thus, as with antigen-specific effector CD8 T cells, NKG2D costimulated RA $CD4^+CD28^-$ T cells. These results imply that NKG2D may contribute to the frequent expansion of these T cells in RA.

$CD4^+CD28^-$ T cells are thought to promote the formation and maintenance of RA inflammatory lesions mainly through IFN-gamma release. IFN-gamma perpetuates synoviocyte pathology, which is associated with secretion of TNF-alpha, IL-15, and tissue-injurious metalloproteinases by synovial fibroblasts and macrophages. We tested whether ligation of NKG2D by $MIC^+$ RA synoviocytes could induce cytokine production by synovial $CD4^+CD28^-NKG2D^+$ T cell clones. T cells were stimulated with autologous or mismatched RA synoviocytes, and release of IFN-gamma and TNF-alpha was measured in the presence or absence of anti-MIC or anti-NKG2D mAbs. Cytokine release was stimulated by the autologous but not the allogeneic synoviocytes and was abrogated by anti-MIC mAb. Anti-NKG2D moderately superinduced cytokine production as previously found with antigen-specific CD8 T cell clones.

Example 6

TNF-gamma and IL-15 Counteract Down-Modulation of NKG2D by Soluble MIC in RA Patient Serum Binding of MIC induces down-modulation of NKG2D, which may normally serve to prevent chronic T cell stimulation and limit autoreactive bystander T cell activation. Many epithelial tumors cause a systemic down-modulation of NKG2D by shedding of soluble MIC, which is presumably mediated by metalloproteinases. Because metalloproteinases are secreted by RA synoviocytes, we tested peripheral blood serum samples from RA patients for the presence of soluble MICA by using an ELISA. Positive results were obtained with all of the ten samples tested, which contained 2.7-30.6 ng/ml (mean 5.8 ng/ml) of soluble MICA. This raised the question of why NKG2D was expressed at high levels on RA $CD4^+CD28^-$ T cells as well as on $CD8^+$ T cells. As expected, incubation of RA patient PBMC with soluble MIC containing serum from a breast cancer patient diminished NKG2D expression on $CD4^+NKG2D^+$ T cells. This effect was abrogated in the presence of the anti-MIC mAb 6D4. By contrast, RA patient serum failed to down-modulate NKG2D because of the presence of TNF-alpha and IL-15. Thus, the ligand-induced down-modulation of NKG2D in RA patients was compensated by the opposite effect of its cytokine-mediated induction.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. A method of treating a patient with rheumatoid arthritis, said method comprising administering to said patient an effective amount of a pharmaceutical composition comprising an inhibitor of an NKG2D receptor wherein the inhibitor is an anti-NKG2D antibody, or an anti-NKG2D Fab, Fab' or scFv antibody.

2. The method of claim 1, wherein said anti-NKG2D antibody is a monoclonal antibody.

3. The method of claim 1, wherein said inhibitor interferes with the binding of an NKG2D ligand to the NKG2D receptor.

4. The method of claim 1, wherein said method further comprises administering a pharmaceutical composition comprising an inhibitory anti-TNF-alpha antibody or an inhibitory anti-IL-15 antibody.

5. The method of claim 1, wherein said patient has an elevated level of NKG2D-expressing T cells.

6. The method of claim 5, wherein said T cells are $CD4^+$.

7. The method of claim 6, wherein said T cells are $CD28^-$.

8. The method of claim 1, wherein said method further comprises a diagnostic step in which, prior to the administration of said inhibitor, the prevalence of NKG2D-expressing $CD4^+CD28^-$ T cells in said patient is assessed, wherein a detection of elevated levels of said cells in said patient relative to a subject who does not have rheumatoid arthritis indicates that the patient is suitable for the administration of said inhibitor.

9. The method of claim 8, wherein said diagnostic step comprises an immunoassay to detect the presence of CD4, CD28, or NKG2D on T cells obtained from said patient.

10. The method of claim 1 comprising providing an effective amount of an anti-NKG2D monoclonal antibody to $CD4^+$ $CD28^-$ $NKG2D^+$ T cells, wherein the autoreactivity of the T cells is reduced.

* * * * *

UNITED STATES PATENT AND TRADEMARK OFFICE
CERTIFICATE OF CORRECTION

PATENT NO. : 7,666,417 B2
APPLICATION NO. : 10/898003
DATED : February 23, 2010
INVENTOR(S) : Spies et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 466 days.

Signed and Sealed this

Twenty-sixth Day of October, 2010

David J. Kappos
*Director of the United States Patent and Trademark Office*